US010888630B2

(12) United States Patent
Baldi et al.

(10) Patent No.: US 10,888,630 B2
(45) Date of Patent: Jan. 12, 2021

(54) MAGNETIC NANOPARTICLES FUNCTIONALIZED WITH CATECHOL, PRODUCTION AND USE THEREOF

(71) Applicant: COLOROBBIA ITALIA S.P.A., Sovigliana Vinci (IT)

(72) Inventors: Giovanni Baldi, Montelupo Fiorentino (IT); Costanza Ravagli, Sesto Fiorentino (IT); Mauro Comes Franchini, San Lazzaro di Savena (IT); Mario Milco D'Elios, Empoli (IT); Marisa Benagiano, Rome (IT); Marco Bitossi, Montelupo Fiorentino (IT)

(73) Assignee: COLOROBBIA ITALIA S.P.A., Sovigliana Vinci (IT)

( * ) Notice: Subject to any disclaimer, the term of this patent is extended or adjusted under 35 U.S.C. 154(b) by 0 days.

(21) Appl. No.: 15/110,189

(22) PCT Filed: Jan. 7, 2015

(86) PCT No.: PCT/IB2015/050122
§ 371 (c)(1),
(2) Date: Jul. 7, 2016

(87) PCT Pub. No.: WO2015/104664
PCT Pub. Date: Jul. 16, 2015

(65) Prior Publication Data
US 2016/0331850 A1 Nov. 17, 2016

(30) Foreign Application Priority Data
Jan. 7, 2014 (IT) .................................. FI2014A0003

(51) Int. Cl.
*A61K 9/00* (2006.01)
*A61K 49/18* (2006.01)
(Continued)

(52) U.S. Cl.
CPC .......... *A61K 49/186* (2013.01); *A61K 9/1075* (2013.01); *A61K 9/20* (2013.01);
(Continued)

(58) Field of Classification Search
CPC .................................................... A61K 49/186
See application file for complete search history.

(56) References Cited

U.S. PATENT DOCUMENTS

2012/0237605 A1   9/2012   Messersmith et al.

FOREIGN PATENT DOCUMENTS

| JP | 2012111694 A | 6/2012 |
| WO | 2008141155 A1 | 11/2008 |

(Continued)

OTHER PUBLICATIONS

Akbarzadeh, Preparation and in vitro evaluation of doxorubicin-loaded Fe3O4 magnetic nanoparticles modified with biocompatible copolymers, International Journal of Nanomedicine, 7, 2012, 511-526.*

(Continued)

*Primary Examiner* — Paul W Dickinson
(74) *Attorney, Agent, or Firm* — Troutman Pepper Hamilton Sanders LLP (Rochester)

(57) ABSTRACT

There are described magnetic nanoparticles the surface of which is functionalized with catechol and constructs comprising a plurality of said nanoparticles encapsulated in a biocompatible polymer matrix, wherein a molecule with therapeutic action is optionally dispersed, said polymer matrix optionally being in turn further functionalized; there are further described cells of the immune system incorporating said polymeric constructs giving rise to their engineering.

14 Claims, 7 Drawing Sheets

(51) Int. Cl.
*H01F 1/00* (2006.01)
*A61K 9/107* (2006.01)
*A61K 9/20* (2006.01)
*A61K 9/50* (2006.01)
*A61K 41/00* (2020.01)

(52) U.S. Cl.
CPC .......... *A61K 9/5031* (2013.01); *A61K 9/5089* (2013.01); *A61K 41/0052* (2013.01); *A61K 49/1857* (2013.01); *H01F 1/0054* (2013.01); *H01F 1/0063* (2013.01)

(56) References Cited

FOREIGN PATENT DOCUMENTS

| WO | 2011/147926 | A2 | | 12/2011 | |
|---|---|---|---|---|---|
| WO | WO-2011147926 | A2 | * | 12/2011 | .......... A61K 9/0009 |
| WO | 2012/177039 | A2 | | 12/2012 | |

OTHER PUBLICATIONS

International Search Report and Written Opinion for corresponding Application No. PCT/IB2015/050122 (dated May 7, 2015).
International Preliminary Report on Patentability for corresponding Application No. PCT/IB2015/050122 (dated Apr. 6, 2016).
Davaran et al., "Preparation and in vitro Evaluation of Doxorubicin-Loaded Fe304 Magnetic Nanoparticles Modified with Biocompatible Copolymers," Internat. J. Nanomed. 7:511-526 (2012).
Cheng et al., "Formulation of Functionalized PLGA-PEG Nanoparticles for in Vivo Targeted Drug Delivery," Biomaterials 28(5):869-76 (2007).
Tran et al., "Promising Iron Oxide-based Magnetic Nanoparticles in Biomedical Engineering," Arch Pharm Res. 35(12):2045-61 (2012).
Translation of Office Action in corresponding Russian Application RU2016132482.
Office Action in corresponding European Application EP15704370.4 dated Feb. 21, 2018.
Wan et al., "Incorporation of Magnetite Nanoparticle Clusters in Fluorescent Silica Nanoparticles for High-Performance Brain Tumor Delineation," Nanotechnology 21:1-8 (2010).
Notice of Reasons for Rejection JP 2016-542675 dated Oct. 2, 2018.
Official Action RU2016132482 dated Sep. 20, 2018.

* cited by examiner

Purification of T cells or other immune cells from peripheral blood or other tissues of the body Selection of specific T cells with antigen Loading T cells with nanoparticles Washing Re-infecting patient H-NMR characterization of the Polymer Starting from right, the following signals can be found: 1.6ppm lactic CH3 - 3.6ppm CH2 PEG - 4.8ppm glycolic CH2 - 5.2ppm lactic CH

UV- VIS R0368/2013

BCA Test mAb Eluate = slq mAb NBR_PTX = 280 μg/mL mAb NBR_PTX = 614 μg/mL

Effective mAb (mAb NBR_PTX - mAb NBR_PTX) = 334 μg/mL

Ratio of mAb/$Fe_3O_4$ = 0.13%

MAGNETIC NANOPARTICLES FUNCTIONALIZED WITH CATECHOL, PRODUCTION AND USE THEREOF

This application is a national stage application under 35 U.S.C. § 371 of PCT Application No. PCT/IB2015/050122, filed Jan. 7, 2015, which claims the priority benefit of Italy Application No. FI2014A000003, filed Jan. 7, 2014, which are hereby incorporated by reference in their entirety.

FIELD OF THE INVENTION

The present invention relates to the field of functionalized nanoparticles, their production and their use.

PRIOR ART

As known, magnetite is a mineral with ferromagnetic properties whose chemical formula is $Fe_3O_4$ (sometimes also written as $FeO.Fe_2O_3$).

It is well known that magnetite in nanoparticle form, i.e. with dimensions ranging from a few nanometers to a few tens, if immersed in a variable magnetic field in the range of radio waves, interacts with the electromagnetic field and then releases thermal energy to what is around it, thus giving rise to what is called hyperthermic effect or magnetic hyperthermia.

In oncology, hyperthermia is exploited to improve the efficacy of chemotherapy or radiotherapy; in fact, raising the temperature of a solid tumor between 41 and 45° C. induces the apoptosis of the tumor cells; generally, this is applied by means of washings with liquids brought to the appropriate temperatures and circulated in the vicinity of the sites affected by tumor masses.

Recently, antennas are adopted which, inserted directly into the tumor mass, generate microwaves and thus interact with the dipole molecules of water, generating hyperthermia.

These treatments are generally extremely invasive and of poor efficacy (in the first case) and not devoid of possible negative side effects such as risk of metastasis, tissue necrosis, etc. in the second case.

Using magnetic nanoparticles that arrive in the immediate vicinity of the tumor tissues or preferably that penetrate into cancer cells, it is possible to overcome the above problems and achieve a high efficiency of the hyperthermic effect, localizing it at the cellular level.

Specifically sending nanostructures in the tumor cells of solid tumors, or on pathological tissues or sites such as Alzheimer's amyloid plaques, or on the damaged tissues of multiple sclerosis, it is thus possible to convey, in an efficient manner and free from side effects, multiple conjugated treatments, such as the hyperthermic and pharmacological ones.

In literature there are many examples of hybrid inorganic-polymer or protein nanoparticles comprising a biocompatible core of nanoparticle magnetite and a coating, either polymer or protein, possibly loaded with drugs and functionalized on the surface, with suitable targeting agents.

These nanoparticles are potential theranostic agents wherein the ability to generate heat under the effect of an electromagnetic EM field (hyperthermic effect), the possibility of drug delivery (DD) and the ability to be identified during its action with imaging techniques (MRI) are synergistically combined.

The International Patent Application WO 2004/071386 describes compounds consisting of mono- or bi-lamellar liposomal microcapsules containing a magnetic nanoparticle and a biologically active molecule having the primary aim to reach and treat liver tumors.

In European patent EP 1 979 365, the Applicant has described constructs consisting of nanometric magnetic particle functionalized with bifunctional molecules wherein an end of said molecules is bound to the surface of the magnetic particle while the other is free and can therefore be reacted with complex units such as biopolymers, cyclodextrins, antibodies and drugs for use in the pharmaceutical and diagnostic field, allowing nanoparticle/binder complexes to be obtained wherein there occurs a total and compact coating of the nanoparticle without significant alterations of the properties depending on it (e.g. optical or magnetic properties).

The subsequent patent EP 2 117 600 describes constructs in which the functionalized particles similar to those described in the above patent EP 1 979 365 are coated with polymers in which a molecule having pharmacological properties has possibly been dispersed.

Also European Patent Application 2 512 992 (to the name of the same Applicant) describes polyol synthesis processes which allow easily obtaining magnetite nanoparticles with even and controlled size (which therefore have a high hyperthermic efficiency).

As can be seen, therefore, many solutions have been suggested in the literature for the solution of the problem of selectively directing within the body particles capable of performing a therapeutic action both by application of hyperthermia alone or in combination with traditional drugs; however, known products do not fully meet the application needs to achieve an effective treatment of tumors and other diseases with nanostructures due to various problems not yet overcome. The first problem is the specificity of the nanostructure, in fact it is known from the literature that hybrid inorganic-polymer/protein particles are quickly eliminated from the reticuloendothelial system when administered systemically (reticular cells, macrophages, Kupffer cells).

The clearance of the nanostructures is therefore responsible for the inefficiency of a nanotheranostic treatment at a systemic level; numerous attempts have been made to overcome this difficulty, including the functionalization of the nanoparticle polymer/protein surface with delivery units such as monoclonal antibodies, peptides and active molecules (such as sugars, etc.) but also in this case, most of the particles are eliminated by the reticuloendothelial system and only a small amount reaches the sites concerned, the tumor tissue and cancerous cells.

A second problem, a consequence of the first one, is that the amount of magnetic particles that reach the tumor or the pathological tissue may prove insufficient to carry out an efficient hyperthermic effect.

Finally, the current nanotheranostic systems have poor stability in biological fluids and thus tend to form large aggregates (up to over 500-1000 nm) that are unlikely to penetrate into the tumor mass or go beyond an intact blood-brain barrier, which worsens the specific targeting of these systems in the target cells, further limiting the efficiency of the treatment.

From the literature it is known that T lymphocytes within the immune system are the main protagonists of the anti-tumor responses.

They are able to selectively recognize the tumor cells due to their specific receptor, called TCR. The T lymphocyte activation by the respective tumor antigenic peptide may occur only if the antigen is presented by the cells represented by monocytes, macrophages, dendritic cells, Langerhans cells, microglia or also B lymphocytes.

For an effective T lymphocyte activation, membrane signals and soluble signals are also required in addition to the antigen. Among the soluble signals, the most powerful activation factor is interleukin 2 (IL-2), while among the membrane signals, the most powerful is molecule B7.

Once the tumor is identified, it is destroyed by the lymphocytes through various mechanisms, among which the main ones are: the cytotoxic machinery linked to perforin and that linked to Fas ligand.

Melanoma was one of the first tumors to be associated with a strong local immune response mediated by T lymphocytes, and over the years it has been possible to prove that a strong T-Lymphocytic response is related to a better prognosis.

Through the use of nanoparticles, it is possible to develop a new custom anticancer strategy based on the use of T lymphocytes specialized in killing a tumor, armed by nanoparticles, ready to hit the tumor, after activation by laser/electromagnetic fields.

Moreover, the literature widely describes the role played by the immune system, and in particular by lymphocytes and inflammatory cells, in diseases of the nervous system such as multiple sclerosis, Alzheimer's disease.

Multiple sclerosis is indeed the prototype of autoimmune diseases in the pathogenesis of which a crucial role is played by T lymphocytes (Elliot M. Frohman, M. D., Michael K. Racke, M. D., and Cedric S. Raine, N Engl J Med 2006; 354:942-955). In particular, T-helper cells capable of producing important inflammatory cytokines, such as interferon-gamma and lymphotoxin, called T-helper cells 1 (Th1), but also T lymphocytes CD8, B lymphocytes and immune cells of the monocyte line, are very important. Also in Alzheimer's disease (Henry W. Querfurth, and Frank M. LaFeria, N Engl J Med 2010; 362:329-344), an important pathogenetic role is carried out by inflammatory mechanisms related to the production of interleukin 1, interleukin 6, tumor necrosis factor α, by microglia and astrocytes, due to amyloid proteins; nanoparticles according to the invention can therefore play an important role also in the treatment of these diseases.

SUMMARY OF THE INVENTION

There are described magnetic nanoparticles the surface of which is functionalized with catechol and constructs comprising a plurality of said nanoparticles encapsulated in a biocompatible polymer matrix, wherein a molecule with therapeutic action is optionally dispersed, said polymer matrix optionally being in turn further functionalized. It was surprisingly found that said polymeric constructs can be incorporated into immune system cells giving rise to the engineering thereof.

DETAILED DESCRIPTION OF THE INVENTION

It has now been surprisingly found that constructs comprising a plurality of magnetic nanoparticles functionalized with catechol encapsulated in a biocompatible polymer matrix can overcome the above problems, ensuring the necessary stability in physiological media and in human blood.

Figure 1:
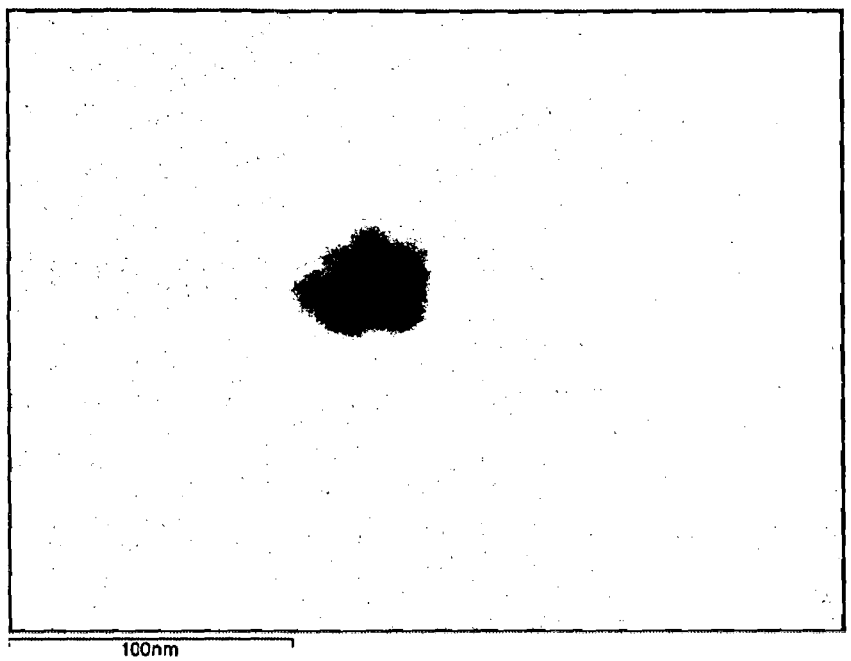
FIG. 1 shows, taken with a Field emission gun scanning microscope in STEM mode, the typical cluster formation taken by the nanoparticles according to the invention within a polymer matrix.

Moreover, the structural features of these constructs helps ensure an implemented hyperthermic effect compared to that shown by monodisperse inorganic cores described in the above patents; this advantage is due to a so-called "cluster structure" (see FIG. 1) of the magnetic particles which tend to combine in structural centers of multiple particles within the polymer matrix carrying out a synergistic effect on the hyperthermic properties.

The functionalization of the magnetic particles with catechol, according to the invention, is essential for the above cluster structure to occur and therefore allows obtaining much superior constructs than those known in the prior art as regards hyperthermic properties and stability over time.

Figure 2:
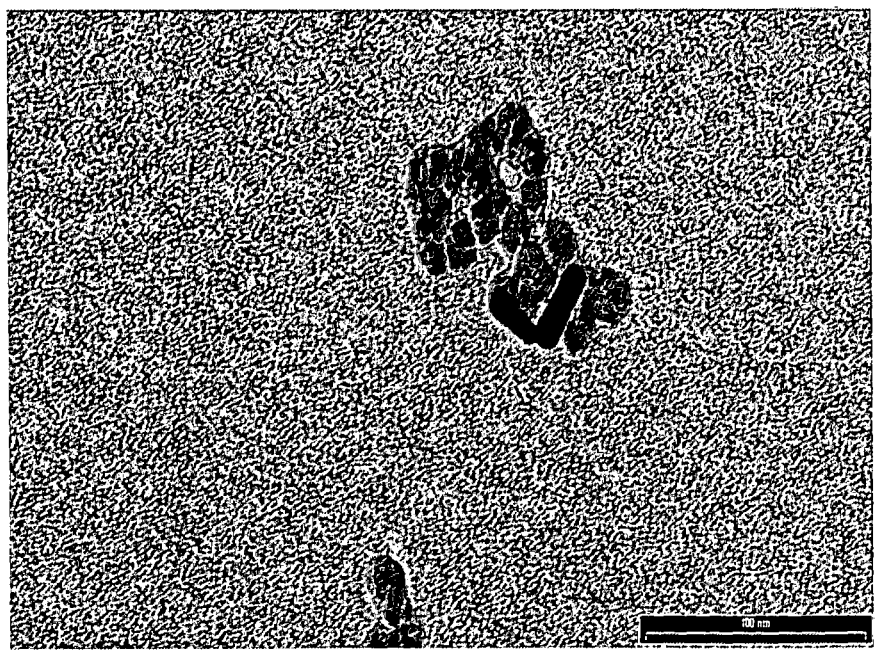
FIG. 2 shows a mixture construct of magnetic particles and gold nanorods.

Among the magnetic particles, magnetite is especially preferred. If preferred, the constructs according to the invention may have, in addition to the magnetic nanoparticles as described above, a plurality of gold nanorods (see FIG. 2). The presence of nanorods allows a considerable hyperthermic effect by applying an infrared laser radiation such as that generated by CO2 lasers, which goes to further increase the hyperthermic effect imparted by cluster structures of magnetite.

This enables a combined laser and radio waves system which uses laser for surface districts or those that can be reached via probe and the radio waves for deep districts.

Magnetic nanoparticles can be prepared through the known polyol process as described for example in the above European patent application 2 512 992 which describes a preparation process in which:
  i) a polyol solution of $Fe^{III}$ is prepared starting from $Fe^{0}$;
  ii) magnetite nanoparticles are prepared in the polyol synthesis conditions.

The above step (i) is the well-known and described reaction of acid attack (also weak acids such as acetic acid) on iron according to the equation:

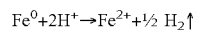

$$Fe^{0}+2H^{+} \rightarrow Fe^{2+}+\tfrac{1}{2} H_2 \uparrow$$

Thereafter, it is possible to completely oxidize the solution of $Fe^{II}$ in polyols to $Fe^{III}$ (for example acetate) through air flushing and addition of $H_2O_2$ in the reaction environment at a temperature of less than 100° C.

Gold nanorods are prepared in known manner with a microwave-assisted synthesis starting from gold in ionic form in the presence of various additives: alkyltrimethylammonium bromide, CnTAB n=10-16, cetylpyridinium chloride, C16 PC and PVP [in this regard, see M. Tsuji, K. Matsumoto, T. Tsuji, H. Kawazumid, Mater. Lett. 59 (2005) 3856] or by reduction of $HAuCl_4$ with ascorbic acid in the presence of CTAB and AgNO3 (in this regards, see Ratto F. et al. *J NANOPARTICLE RESEARCH* 2010 and [Ratto F. et al. *J NANOPARTICLE RESEARCH* 2012)

The surfaces of the magnetic and/or magneto-optical particles obtained as described above are functionalized with catechol (bifunctional group) by exploiting the affinity of the polar groups OH to the surface of the particles and allowing the end part not bond to the particle surface to maintain a hydrophobic reactivity suitable for the subsequent incorporation in a polymer/protein matrix.

The polymer matrix according to the present invention is understood to consist of biodegradable copolymers and is thus capable of allowing the release of the drug, which must proceed gradually as the matrix degrades in a physiological environment.

Examples of suitable copolymers for the purpose are: biodegradable nanomicelles, polyesters, polyesters, polyurethanes, polycarbonates and poly(glutamic) acid, polyetheramine and polybenzylglutamate.

Particularly preferred are biodegradable nanomicelles, consisting of block copolymers of poly(lactic-co-glycolic) acid and polyethylene glycol carboxylate (PLGA-b-PEG-COOH, MnPLGA range=44-10 kDa, MnPEG=2-3 kDa) having formula (I)

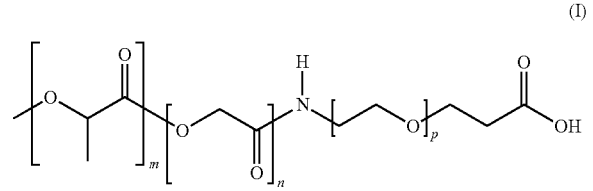

wherein m=[117-330]; n=[117-330]; p=[60-100].

This product is known and has already been employed in various other works of Drug Delivery also at the level of Clinical Phase I for testing of anticancer agents (see X. Shuai et al, 2004 and X. Shuai, H. Ai, N. Nasonkla, S. Kim, J. Geo, J. Controlled Release, 2004, 98, 415).

Figure 3:
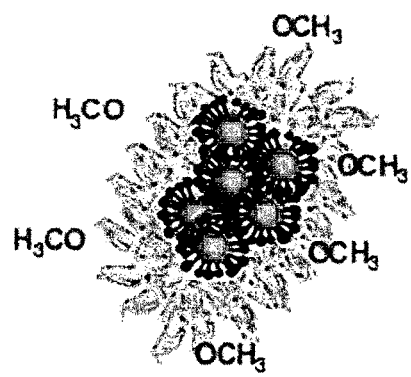
FIG. 3 schematically shows a construct model consisting of nanoparticles of magnetite or magnetite and gold nanorods and coated with block polymers PLGA-b-PEG-COOH.

The polymer in fact has features that allow assembling nanospherical systems with a hydrophobic inner area, guaranteed by residues of PLGA, and a hydrophilic outer area which is imparted by the terminals of PEG-COOH (see FIG. 3).

This dual feature allows the nanospheres to trap the organic active ingredients in the hydrophobic part and to be dispersed in aqueous solution thanks to the hydrophilic part.

If desired, the polymer can be admixed with molecules having a therapeutic action which is dispersed in the polymeric matrix according to known processes and as illustrated in the examples given below.

Examples of molecules with therapeutic action according to the invention are for example anti-cancer drugs (taxanes, gemcitabine, vincristine, etc.), peroxynitrite scavengers, superoxide dismutase inhibitors, retinoids (bexarotene), cytokines such as interleukin 10, TLR-ligands such as the HP-NAP molecule capable of activating TLR2, aspirin.

In addition, the carboxylic acid functionality of the PEG-COOH fragment of the micelles allows a chemical stable bond with monoclonal antibodies, proteins, peptides or active molecules of interest (for example, and/or fluorescent dyes) for the specific recognition by the cellular overexpressions.

Among the antibodies useful for the functionalization according to the invention we may mention hERG, hEGFR, IgG, moAb, etc.

The examples (see example 10) describe the above functionalization, in particular using a specific monoclonal antibody hERG1 described and claimed in Italian patent IT 1,367,861.

In particular, it is a specific monoclonal antibody against the extra-cellular portion S5-pore of protein HERG1 produced by a hybridoma comprising the product of a fusion between an immortalized cell, belonging to the murine neoplastic cell line NSO, and a lymphocyte obtained by immunization of a mouse with a peptide of sequence EQPHMDSRIGWLHN.

The construct according to the invention (hereinafter also referred to as "nanobioreactor" or "NBR") containing magnetic nanoparticles functionalized with catechol is prepared by carrying out a nanoprecipitation, wherein two fluids:
- an organic solution of polymer dissolved in a solvent, mixed with the suspension of nanoparticles coated with organic binder, both in the same solvent, and
- an aqueous solution of Na2HPO4 1 mM) are mixed in a constant flow in a mixing cell with batch or continuous synthesis.

For the batch synthesis, the organic suspension containing polymer and particles is injected with a syringe in the aqueous solution, without magnetic stirring, in a single step.

For the continuous synthesis, a double peristaltic pump system is prepared to carry out the addition of the organic solution to the aqueous stream (organic volume/water ratio 1/10). The respective tubes draw the solution directly from the lungs containing the organic suspension (with functionalized particles and polymer) and the solution of $Na_2HPO_3$ 1 mM (pH 7.4).

Once the dispersion of hybrid particles (consisting of magnetic nanoparticles functionalized with catechol included in the polymer) has been obtained, part of the organic solvent is removed via a rotary evaporator so as to minimize the amount of organic phase in the subsequent production steps.

The suspension is then dialyzed against aqueous solution $Na_2HPO_3$ for the removal of the organic phase and concentrated to the minimum volume possible to obtain a concentration of from 0.1 to 1% w/w.

Through a second concentration it is possible to obtain a much more concentrated product through membrane dialysis with a theoretical concentration factor ranging from 5× to 20× depending on usage. The product is then filtered with a filter to 0.22 µm to remove the bacterial load. The product has an excellent hyperthermic efficiency if irradiated for 30 minutes with alternating magnetic field of 21-24 kA/m and a frequency of 160-190 kHz, its temperature increases by at least 5° C. The method described herein allows the preparation of constructs with a dimensional distribution centered in a range from 30 to 60 nm.

The potential ξ of the product thus obtained (Malvern Zetasizer nano-S), measured to have information about the electrostatic stability of the suspension and its ionic strength, is lower than −30 mV, which means that the particles are affected by the negative surface electrostatic repulsion produced by the carboxylic groups which at (physiological) pH 7.4 are partially deprotonated.

The experimental conditions described above allow making a suspension with good stability after dilution into culture media typically used for cell cultures (DMEM, RPMI), exhibiting little tendency to aggregation and sedimentation also after a clear change in ionic strength conditions due to dilution.

Obtaining the product functionalized on the surface with monoclonal antibodies and/or fluorescent dyes (e.g. Cyanine®, Dylight®, etc.) for a targeted delivery and for use in imaging techniques requires the use of NBR as a precursor before it is subjected to the second concentration process (see above).

Typically, at this stage, the product has a concentration of about 0.05-0.1% wt. of inorganic material.

The preliminary process step provides the activation of the end carboxyl groups of the polymer, exposed towards the outer part of the nanoparticle, in contact with the polar phase, with activators such as EDAC [1-ethyl-3-(-3-dimethylaminopropyl) carbodiimide hydrochloride] (molar ratio EDAC/COOH=10/1) and sulfo-NHS (NHS/COOH=1/1), so as to promote the subsequent attack by esterification of the end amine groups of the monoclonal antibody and/or of the fluorescent dye.

In the case of fluorescent dyes with emission at $\lambda$600-800 nm (suitable for NIR imaging applications in vivo), since only NHS ester-terminal molecules are available on the market, it is necessary to provide for an intermediate step where a diamino-terminal linker is added for the bridge link on the one hand with the fluorescent dye, and on the other with the carboxylic groups of the activated polymer.

Once the surface of nanoparticles has been activated, the antibody and/or amino-terminal dye solution is added and let stand.

The suspension is then concentrated and dialyzed against aqueous $Na_2HPO_3$ and concentrated up to 0.2-1.0% wt. of inorganic phase, depending on usage.

The product is then filtered with a filter to 0.22 µm to remove the bacterial load.

The method described herein allows the preparation of constructs with a dimensional distribution centered in a range from 40 to 70 nm.

The potential $\xi o \varphi$ the product thus obtained (Malvern Zetasizer nano-S), measured to have information about the electrostatic stability of the suspension and its ionic strength, is less than −30 mV, but greater than that measured on the NBR product, which means that the negative charge exerted by the carboxylic groups of the raw product is partly neutralized by the bound antibody/dye.

The contents of antibody bound to the particles is analyzed using the BCA® test: following the addition of suitable reagents to the solution containing the protein analyte, a complex of $Cu^{2+}$ develops whose coloring at 562 nm is observed with spectral analysis and from which the concentration of antibody is derived using a linear calibration.

With the procedure described herein it is possible for example to produce nanoparticles functionalized with moAb, with moAb attack percentage between 5 and 30% wt compared to the inorganic phase content.

The production of the nanobioreactor/lipophilic drug (hereafter NBR_PTX) and nanobioreactor/antibody/lipophilic drug (NBR_hERG_PTX) system (where the lipophilic drug for example is Paclitaxel) is exactly the same as the synthesis process of the nanobioreactor as described above and therefore provides for the encapsulation of the inorganic nanoparticles, previously functionalized with catechol, within a polymeric matrix based on PLGA-b-PEG-COOH. The only variation to this process provides for the dissolution of the specific amount of drug within the polymer and the suspension of the functionalized nanoparticles.

Then, the nanobioreactor loaded with paclitaxel (NBR_PTX) is obtained using the nanoprecipitation method, where the aforementioned organic solution is vigorously added to the aqueous solution of $Na_2HPO_4$ 1 mm inside a mixing cell. There are no changes in the morphological properties of the suspension from a batch synthesis to a continuous one. The purification, filtration and concentration processes applied are the same as described above.

For the product characterization, in addition to the determination of the average particle diameter, their potential $\xi$ and the concentration of inorganic phase, the amount of active ingredient encapsulated is also determined by high performance liquid chromatography.

The product thus obtained and characterized can then be further functionalized on the surface with targeting units such as (hEGR, hEGFR, IgG, . . . ).

The process set up to this end accurately follows the targeting procedure of the nanobioreactor NBR_moAb as described above.

In fact, it provides for a preliminary step of activation of the carboxyl groups present on the polymer, with activators such as EDAC and sulfo-NHS and a step of reaction with the monoclonal antibody, all according to the same proportions as set out in the process previously described for the NBR_moAb.

The usual purification and characterization processes are then performed. The nanoparticle suspensions thus obtained are characterized by a mean hydrodynamic diameter of between 45 and 55 nm, while the potential 4 is well below −30 mV.

According to a further embodiment of the invention, the constructs as defined above, as an alternative to the decoration with proteins or with antibodies, may be incorporated into cells of the immune system.

Surprisingly, the constructs comprising clusters of magnetite particles functionalized with catechol and coated with block copolymers of poly(lactic-co-glycolic) acid and polyethylene glycol carboxylate (PLGA-b-PEG-COOH, MnPLGA range=44-10 kDa, MnPEG=2-3 kDa) as described above are easily incorporated by cells of the immune system without compromising their functionality and vitality.

Once the immune system cells are engineered with the introduction of the constructs according to the invention, these can be used for the diagnosis of tumor diseases, degenerative diseases (e.g. Alzheimer's disease), of the central nervous system, cerebral cardiovascular and infectious diseases, transplants, autoimmune diseases and also for the therapy of tumors, cerebral cardiovascular diseases, degenerative diseases (e.g. Alzheimer's disease), infectious diseases, transplants, liver cirrhosis and other conditions involving fibrogenesis, diseases characterized by multiple abortions, intrauterine fetal death, neonatal diseases, congenital and acquired coagulation disorders, genetic diseases, autoimmune diseases, and finally for pain relief.

The induction of the release can take place with different methods, such as the specific antigen (e.g. MAGE-3 in the case of treatment of melanoma, MOG or myelin antigens in the treatment of multiple sclerosis, etc.) or with appropriate immunomodulatory substances such as IL-2, CD40 ligand, TLR-agonists, liposomes, immunostimulating complexes (ISCOMS).

It should be noted, in fact, that an important property of the cells of the immune system is represented by their ability to reach almost all the districts of the body, therefore, their use as a carrier to reach specific districts, carrying through the construct according to the invention the particular product required to the destination, exceeds the great current limitation of the nanotheranostics represented by the low specificity of the treatment.

The cells of the immune system useful for the above purpose are for example selected from:

T-lymphocytes, monocytes, macrophages, dendritic cells, natural killer cells, B-lymphocytes, neutrophil granulocytes, eosinophil granulocytes, basophil granulocytes, gamma delta cells.

The cells are taken from the single patient, loaded with the desired nanoparticles and then re-introduced in the same patient topically or systemically.

The cells of the immune system will then be purified, as described below, and in order to facilitate the selective/preferential targeting of the body districts affected by the disease in question, the cells can be treated ex vivo with relevant antigens (or allergens), immunomodulatory drugs or engineered with immuno potentiating or immuno suppressive molecules.

One of the ways to select T cells for diagnostic or therapeutic purposes is to enrich the number of T lymphocytes specific for a particular antigen which can be a tumor antigen as described above.

Lymphocytes, properly engineered with the constructs of the invention, can, once in place, release the particles by means of suitable chemical stimuli, the particles can then under irradiation of electromagnetic fields in the range of radio waves exert hyperthermia or release active ingredients such as antitumor drugs, scavengers of molecules active in the oxidative stress of brain tissues, anti-inflammatory molecules, etc. Nanoparticles can still perform their functions even if they remain confined within the lymphocytes themselves.

The magnetic nanoparticles can also perform the MRI imaging function, being excellent T2 T2* contrast media (see the above patents), nanoparticles containing gold nanorods may be used in laser-mediated antitumor therapy and identified by methods of the photoacoustic spectrometry type.

Purification and Selection of Lymphocytes

T lymphocytes for use against tumors are purified from the peripheral blood or from the tumor site or from the patient's lymph nodes after prior administration of the relevant tumor antigens, or from other districts of the body as deemed relevant, using standardized methods and/or with the aid of selective MACS® methods (Current Protocols in Immunology 2013; D'Elios et al J Immunol 1997; 158:962-967).

In order to select T lymphocytes specific for the tumor, T lymphocytes are placed in culture with the relevant tumor antigen (e.g. MAGE-3 for melanoma, at a concentration of 10 μg/ml) in complete RPMI medium for five days. Then, recombinant human IL-2 is added every three days, and then the cells will be loaded with nanoparticles, washed and then administered to the patient topically and/or systemically.

T cells for use as diagnostic product, for example for multiple sclerosis with magnetic resonance technology, are selected for their specificity for myelin antigens or MOG (10 μg/ml) or other antigens as preferentially capable of achieving the structures of the CNS.

To this end, they are cultured with one or more antigens for five days, then expanded with IL-2, and then loaded with NP.

The same procedure can be used for other neurological diseases, such as Alzheimer's disease, Parkinson's disease, stroke and other cerebro-cardiovascular diseases using appropriate relevant antigens.

Dendritic cells (highly efficient for their ability to present the antigen to T lymphocytes, and thus greatly able to activate T-lymphocytes) are obtained using traditional standardized methods and/or with the aid of selective methods MACS® (Current Protocols in Immunology 2013; Codolo et al. Arthr Rheum 2008; 58:3609-17). They will be incubated for 36-44 hours with the desired antigen, then loaded with NP, washed and reinfused to the patient for therapeutic or diagnostic purposes (see the process layout in FIG. 5).

Natural killer cells and/or gamma delta lymphocytes, with strong cytotoxic activity, are obtained using traditional standardized methods and/or with the aid of selective MACS® methods (Current Protocols in Immunology, 2013), they are then loaded with the desired NP as well as possibly with other immunomodulatory compounds, washed and reintroduced into the patient for therapeutic (e.g. antitumor) or also diagnostic purposes.

The neutrophil granulocytes are obtained using traditional standardized methods and/or with the aid of selective MACS® methods (Current Protocols in Immunology, 2013), they are then loaded with the desired NP as well as possibly with other immunomodulatory compounds, washed and reintroduced into the patient for diagnostic (e.g. to identify the presence of any foci of infection in the body which cannot be identified by other techniques) or also therapeutic purposes. Also other cell types may be selected for diagnostic and/or therapeutic use (such as effector cells to be used for the therapy of tumors, autoimmune diseases, infections, degenerative diseases), such as B lymphocytes, eosinophils, basophils, which are obtained using traditional standardized methods and/or with the aid of selective MACS® methods (Current Protocols in Immunology 2013).

They are then loaded with the desired NP or possibly with other immunomodulatory compounds, washed and re-introduced into the patient. Immune cells loaded with nanoparticles can be used to display with appropriate imaging techniques body districts that are a location of the disease.

T cells and Jurkat cells are optimally filled with NP after 4 hours. Monocytes/macrophages, dendritic cells, J774A.1 cells are capable of incorporating the nanoparticles with a method according to the invention in which monocytes/macrophages, dendritic cells, J774A.1 cells are loaded with the nanoparticles (NP) at a concentration of 0.05% in a suitable specific culture medium (mmedium). To form the mmedium containing NP, the NP are first dispensed and then the specific culture medium.

The mmedium consists of:

COMPLETE DMEM 10% FBS

COMPLETE DMEM:

DMEM HIGH Glucose (DME/HIGH). (EUROCLONE) (code: ECB7501L)

L-GLUTAMINE, solution 200 mM (100×). (EUROCLONE) (code: ECB 3000D)

PENICILLIN-STREPTOMYCIN Solution (100×). (ATCC) (code: 30-2300)

10% fetal bovine serum FBS: Fetal Bovine Serum, Qualified. (Sigma-Aldrich) (code: F6178-100 mL)

Where necessary, autologous serum of the patient or media in the absence of serum will be used instead of fetal bovine serum.

Monocytes/macrophages, dendritic cells, J774A.1 cells are optimally filled with NP after 2 hours but the incorporation phenomenon is active after 15' up to 24 h.

Figures 5, 6:
FIG. 5 shows the layout of the process for the purification and selection of lymphocytes.
FIG. 6 shows a picture taken with an optical microscope of monocytes/macrophages charged with nanoparticles according to the invention.
Figure 7:
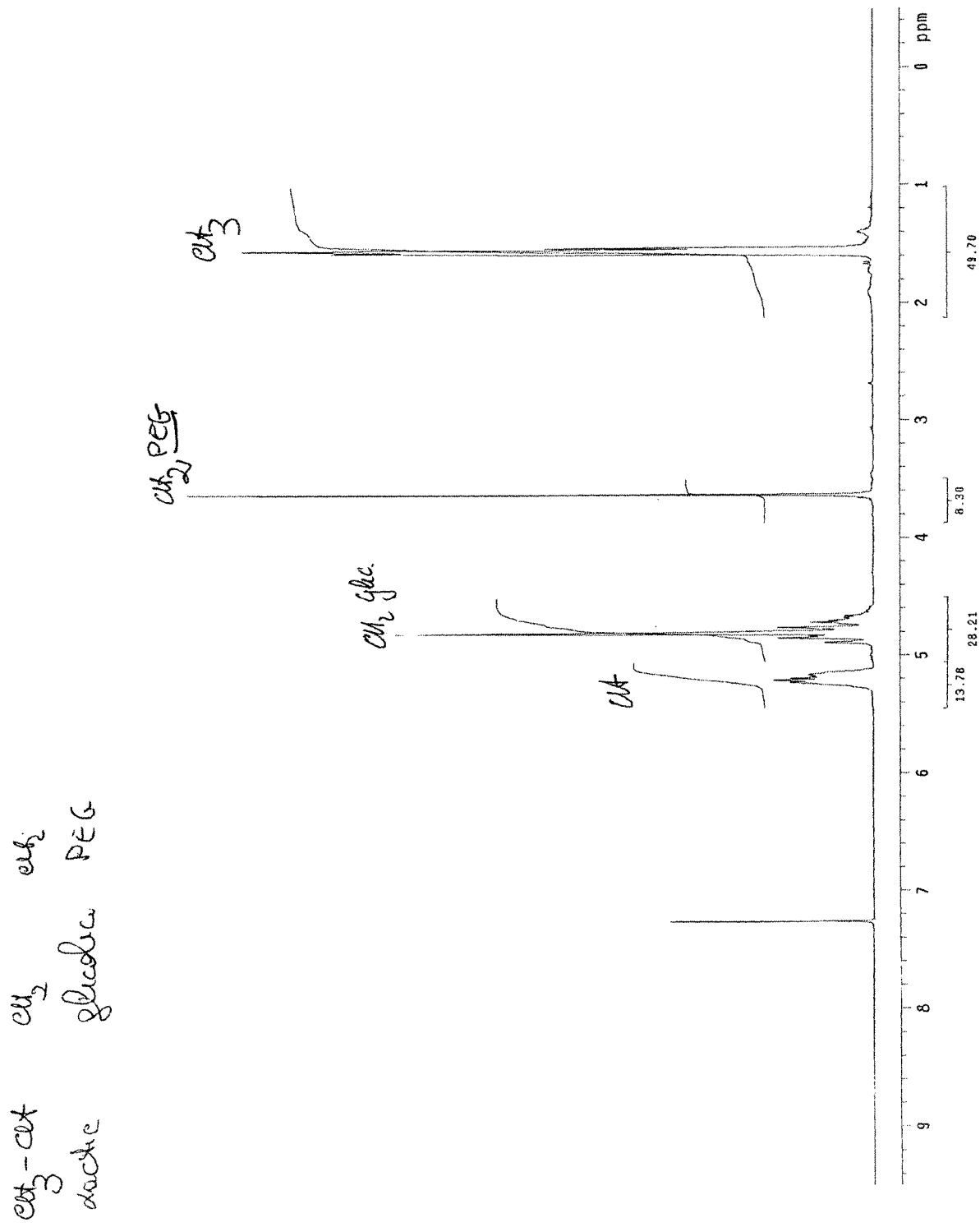
FIGS. 7 and 8 show the 1H-NMR of the polymer PLGA-NHS conjugated with NH2-PEG-COOH.
Figure 8:
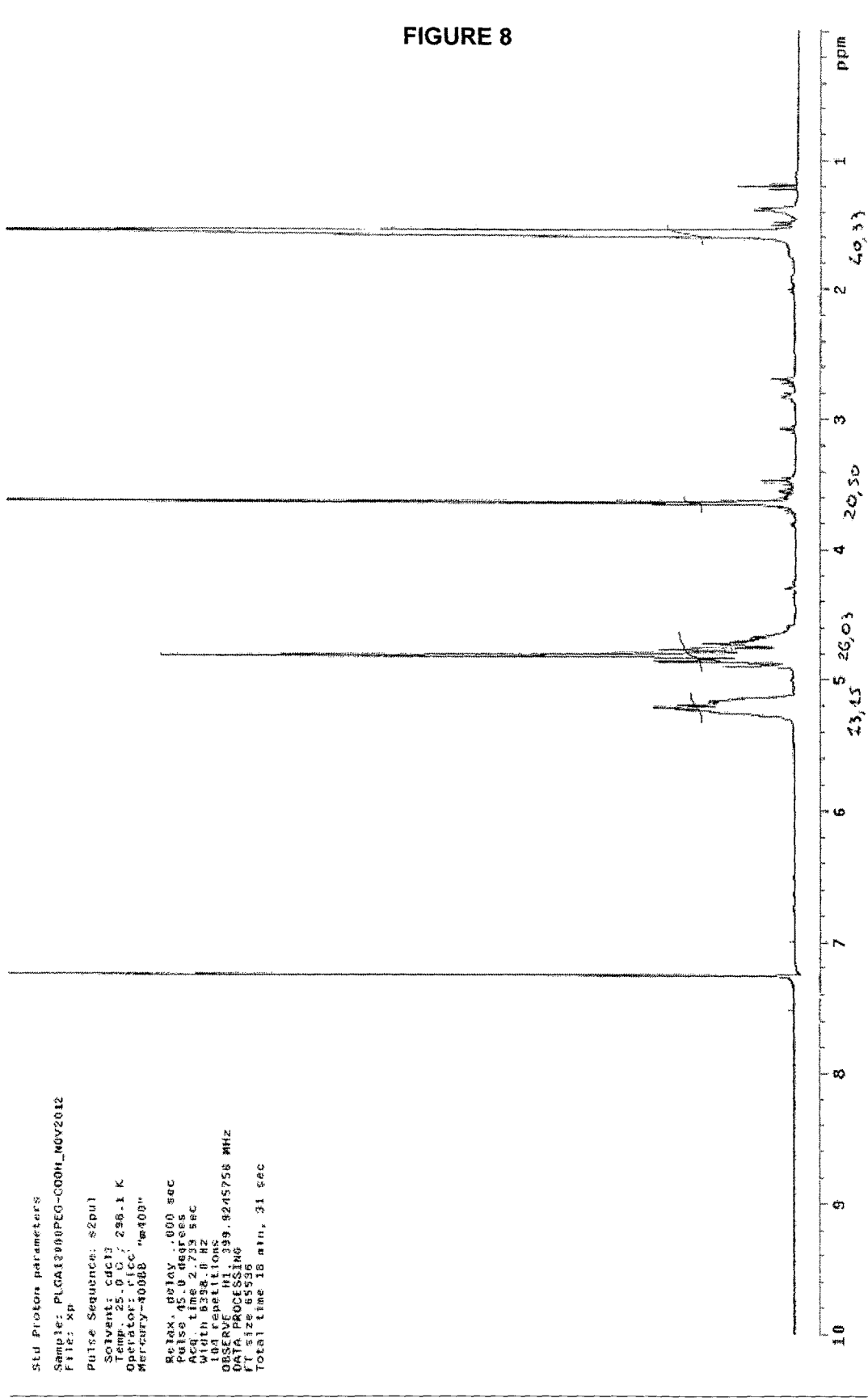
Figure 9:
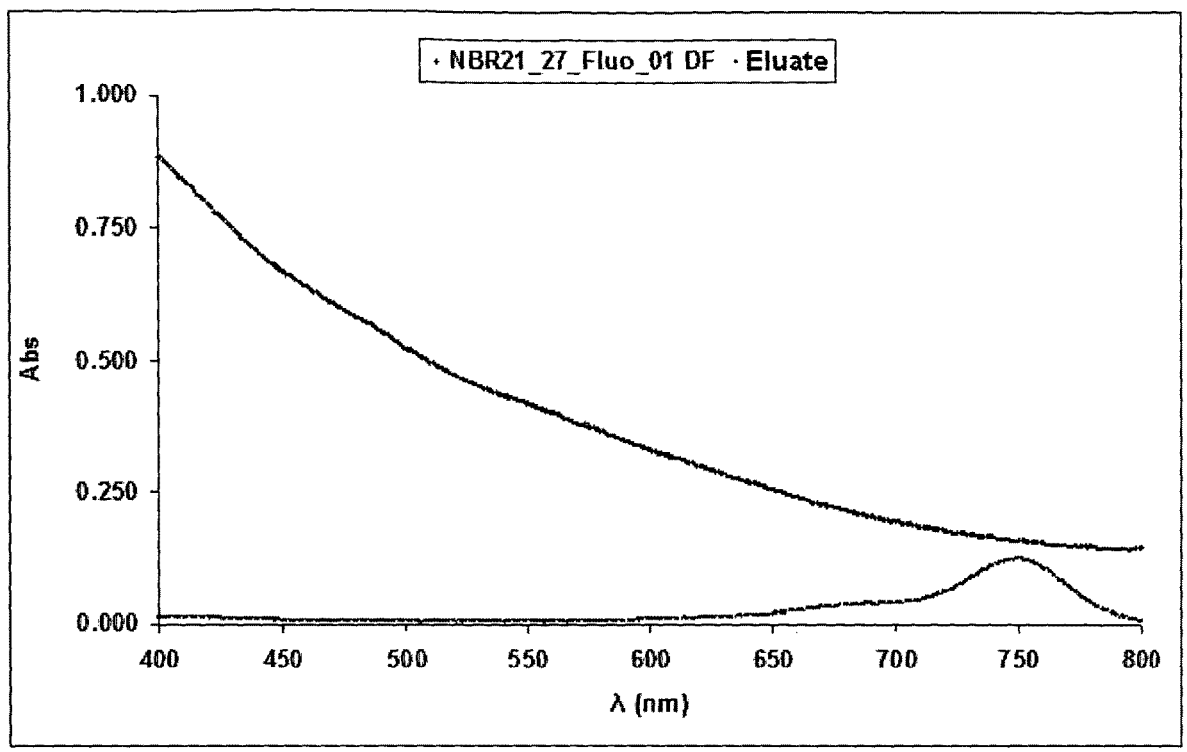
FIG. 9 shows the UV-Vis spectrum of a product according to the invention.
Figure 10:
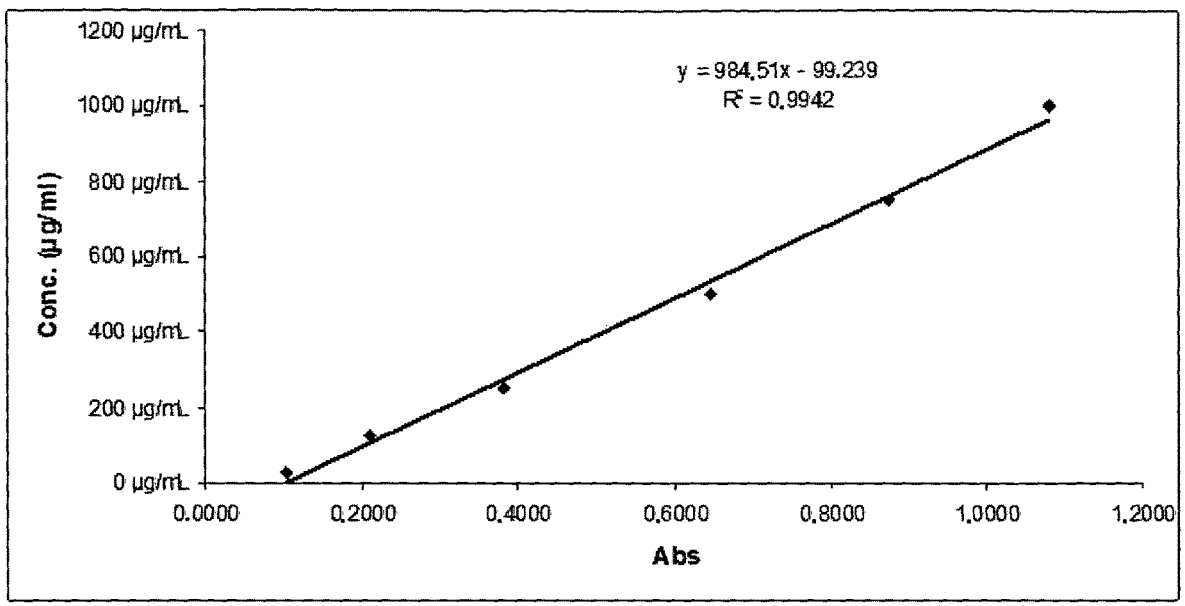
FIG. 10 shows a BCA Test on a product according to the invention.

FIG. 6 shows a picture taken with an optical microscope of the monocytes/macrophages charged with nanoparticles.

Figure 4:
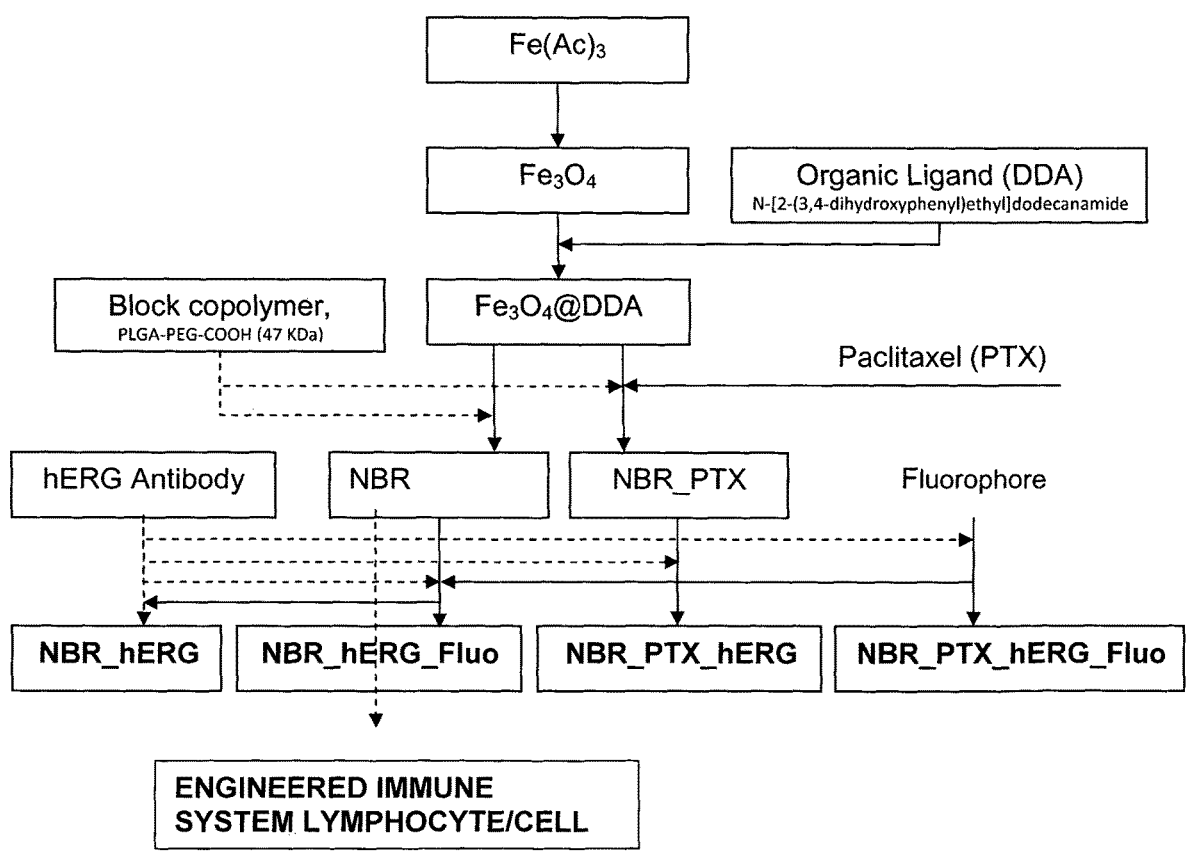
FIG. 4 shows the layout of the step by step preparation process of the nanostructured construct according to the invention.

The invention will be more and better understood in the light of the examples given below, also noting FIGS. 4 and 5 which schematically summarize the various steps for the preparation of the construct and the engineering of the cells of the immune system.

Example 1

Preparation of Iron Acetate in Diethylene Glycol DEG

Reagents:

40 g Fe (Fe<99%<212 mm) equal to 0.716 mol; 800 g water; 800 g CH3COOH (80%) equal to 10.67 mol; 46.64 g oxygenated water (30%) equal to 0.41 mol; 0.12 g concentrated HCl; DEG (diethylene glycol) 3850 g.

Synthesis:

Iron, the acetic acid and water solution and the hydrochloric acid were loaded to a 5000 mL 4-necked flask under nitrogen flow and the temperature was brought to 90° C. and maintained for 6 hours. The system was left to cool under N2 and the solution was filtered to remove the undissolved Fe. The oxygenated water is added dropwise to the clear solution placed in a flask using a dripper, keeping the temperature at 35° C. for 1 h, obtaining a clear solution equal to 1628.3 g having an iron titer of 2.40% w/w. Excess acids are then stripped by a first vacuum distillation at the T of 40°, a recirculation of the dry part with water and removal by distillation two times (two consecutive washes) and a final stripping at the T of about 50°. 3850 g DEG are added to the dry so as to bring the theoretical iron titer to the value of 1.01% w/w Fe.

Example 2

Preparation of $Fe_3O_4$ Nanoparticles in Diethylene Glycol

Reagents:

1.50 g $Fe^0$ ($Fe^0$<99%, <212 mm) $Fe^0$=0.179 mol; 150 g DEG; 1.2 g solution in DEG 1/10 HCl conc. 37%; 300.00 g FeAc3 in DEG (1.01% w/w $Fe^{III}$).

The metal iron and DEG were placed in a 500 mL 4-necked flask under $N_2$ and the temperature was brought to 150° C. The solution in DEG of hydrochloric acid was added to the system and left under stirring for 5 minutes. Iron acetate is then added in 10 equivalent aliquots, using a syringe, so as to ensure the correct growth of the particles, bringing the temperature to 170° C., the reaction ends within 24-36 hours.

The product was left to cool to 60° C. and decanted in a beaker, magnetically retaining the unreacted metal iron and then filtered on a 0.45 μm glass fiber. 450 g of a nanosuspension of magnetite in diethylene glycol having a titer in ionic Fe equal to 0.91%±0.05, which expressed in $Fe_3O_4$ corresponds to 1.253%±0.05. Hyperthermia was measured on this sample and the values were as shown in the table

| Sample | Field KA/m | Frequency KHz | Starting T°(C.) | $SAR_M$ |
|---|---|---|---|---|
| Filtered Fe3O4 | 24 | 168 | 29.4 | 350.0 |

$SAR_M$: Specific absorption rate expressed on the mass of metal (Fe)

Example 3

Preparation of Organic Binder N-(3,4dihydroxyphenethyl)dodecanamide (DDA)

MW=335.48 g/mol

Reagents:

25 g Dopamine hydrochloride equal to 0.1318 mol; 1 L THF; 45 mL Triethylamine 0.32 mol; 31.20 mL Lauroyl chloride 0.135 mol;

Purification and Crystallization 400 mL THF (Aldrich 401757-2L-Lot STBC4923V)

935 mL ethyl acetate (Aldrich 34972-2,5L-Lot 57BC011AV)

315 mL petroleum ether (Aldrich 77379-2,5L-Lot BCBG7367V)

Synthesis:

To a 5L 4-necked flask, dopamine hydrochloride and then THF (1 L) are placed under nitrogen atmosphere and then the triethylamine is added, and the system is kept under stirring for about 20' to obtain a white suspension.

To a 3 L flask with a flat bottom, THF (1 L) and the acylating agent are added. The solution is stirred and added to the reagents contained in the 5 L flask using a peristaltic pump at a rate of approximately 2 mL/min over 9 h, obtaining a solution of yellow-orange color with some white solid on the bottom.

Purification:

The organic phase that contains the synthesis product is then purified and the latter is recovered from the by-product formed during the reaction. The purification is carried out through the removal of the solvent via rotavapor with two recirculation's (2×200 mL). On the other hand on the solid residue, and on the residual traces in the synthesis flasks, aqueous extraction and treatment with ethyl acetate are carried out in a separating funnel. The organic phases are all combined, dried with Na2SO4 and finally brought to dryness in a rotavapor. 57 g of orange oily product are obtained.

Crystallization:

450 mL of a mixture of petroleum ether:ethyl acetate=7:3 are added to the product. The suspension was put under cold water and a white solid began to crystallize. The system was left 1 day to rest.

The solid was filtered on a Buckner, washed with mother liquor and dried using an oil pump. About 39 g were obtained (44 g theoretical—yield 88.6%).

The mother liquor resulting from crystallization (2.45 g—orange brown solid) and from the washes were brought to dryness (PRIME 27.13 g—dark brown solid).

Example 4

Surface Functionalization of Fe$_3$O$_4$ Nanoparticles (in THF)

Reagents:
40.0 g Fe$_3$O$_4$ dispersion equal to $2.164 \cdot 10^{-3}$ mol; 1089 mg DAA equal to $3.247 \cdot 10^{-3}$ mol; 120 mL EtOH; 80.0 g THF.

1089 mg DDA in 120 mL EtOH are solubilized in a 250 mL flask; the solution thus prepared is added to magnetite with a 60 ml syringe. It is then sonicated for 1 h in an ultrasound bath. The sample is left to stand for a few minutes and then 60 mL H$_2$O are added and the NP are settled on neodymium magnet; the supernatant is separated and nanoparticles are dispersed again in 80.0 g THF. 4 drops of triethylamine are added to the dispersion (the particles disperse after about ten minutes).

Characterization
DLS

| SAMPLE | PDI | Z-ave | Dv1 | % V1 |
|---|---|---|---|---|
| Fe3O4-DDA | 0.142 | 34.9 (±0.4) | 27.1 (±0.5) | 100 |

Example 5

Surface Functionalization of Fe3O4 Nanoparticles (in Acetone)

Reagents:
4.0 g Fe$_3$O$_4$ dispersion equal to $0.2 \cdot 10^{-3}$ mol; 108.0 mg DAA equal to $0.3 \cdot 10^{-3}$ mol; 12.0 mL EtOH; 13.6 mL acetone.

The suspension of magnetite is sonicated in an ultrasonic bath for 1 h, then it is added to a solution of 108 mg DDA in 12.0 mL EtOH with a 25 mL syringe. Then, it is placed to sonicate for 30 min. The specimen is left to rest for a few minutes. 6 mL H$_2$O are added and NP are settled on neodymium magnet, then the supernatant is separated and the NP dispersed again in 13.6 mL acetone. 2 drops of triethylamine are added to the dispersion (the particles disperse immediately).

Characterization
DLS

| SAMPLE | PDI | Z-ave | Dv1 | % V1 |
|---|---|---|---|---|
| Fe3O4-DDA | 0.218 | 34.5 (±0.2) | 22.4 (±0.5) | 100 |

Example 6

Synthesis of Polymer PLGA-b-PEG-COOH 43-3 kDa

For the synthesis of the block copolymer PLGA-b-PEG-COOH, the precursor PLGA-COOH (MW 44-10 kDa) was activated with N-hydroxysuccinimide (NHS) using the coupling chemistry of dicyclohexylcarbodiimide (DCC), and then combining the adduct with the amino-functional part PEG-NH$_2$ (MW 2-3 kDa) in dichloromethane (DCM) as described hereinafter:

Step 1: Activation of the Carboxylic Functionality with NHS

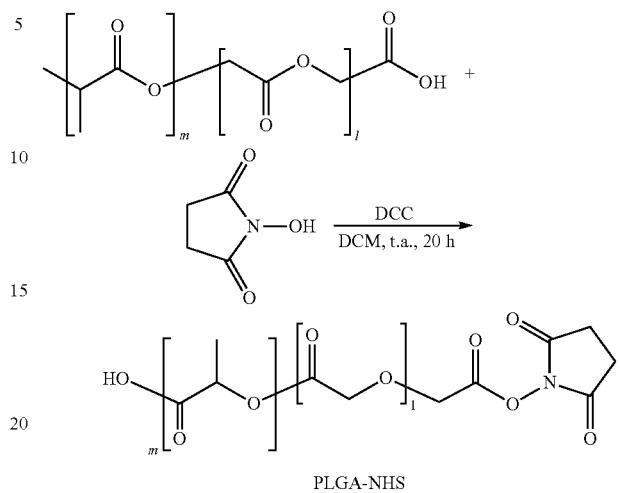

PLGA-NHS

Reagents

| 98 g | PLGA-COOH (50:50 Poly (DL-Lactide-co-glycolide), Carboxylate End Group |
| 1.037 g | NHS (N-hydroxysuccinimide 98%) |
| 720 mL | DCM (Dichloromethane >99.9%) |
| 1.98 g | DCC (N,N Dicyclohexylcarbodiimide 99%) |
| 990 mL | DCM (Dichloromethane >99.9%) |
| 1600 mL | Diethyl ether (≥99.8) |

Process

PLGA-COOH and 600 mL dichloromethane were added to a 5L four-necked flask under nitrogen. After solubilization of the polymer, N-hydroxysuccinimide (NHS) and then N,N Dicyclohexylcarbodiimide (DCC—about 0.25 g at a time) were added; the system was left under stirring for about 40 h in an inert atmosphere. 120 mL dichloromethane were used to wash the funnel from the solids in order not to lose the raw materials.

The yellow suspension was filtered into a 2L tailed flask in order to remove dicyclohexylurea. The 5 L flask was washed with 250 mL (×3) and 190 ml CH$_2$Cl$_2$. The product was concentrated to approximately 400 mL volume by a rotavapor in a 1 L flask (50 ml dry DCM wash): a dense yellowish suspension was obtained. The PLGA-NHS was precipitated using 400 mL (×4) of cold diethyl ether. For each wash, the white solid was decanted and the supernatant was removed. Subsequently, the solid is dried for about 2 h30' using the oil pump.

Step 2: Conjugation of PLGA-NHS with NH2-PEG-COOH

PLGA-NHS

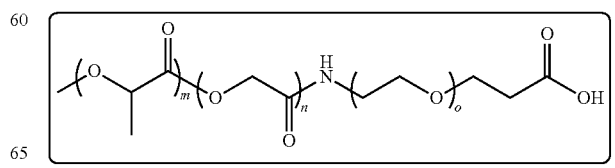

CHCl₃
CH₂Cl₂-PM=119.38
DIPEA N-Ethyldiisopropylamine [(CH3)2CH]2NC2H5-PM=129.24 COOH-PEG-NH₂ HCl×NH₂-PEG-O—C₃H₆—COOH-PM PEG=3000 da Reagents
PLGA-NHS (reaction intermediate)

| | |
|---|---|
| 1 L (synthesis) | CHCl₃ (Chloroform ≥99.5) |
| 100 mL + 250 mL (washes) | CHCl₃ (Chloroform ≥99% stab. with 0.75% ethanol) |
| 1.2 mL | DIPEA (N,N-Diisopropylethylamine 99.5%) |
| 7 g | COOH-PEG-NH₂ (Polymer-hydrochloride form ratio) |
| 1250 mL | Diethyl ether (≥99.8%) |
| 1250 mL | Deionized water |

Process

In a 2L 3-necked flask equipped with mechanical stirrer, under nitrogen flow, the resulting intermediate was dissolved in 1 L chloroform. 1.2 mL DIPEA were added to the system using a syringe and subsequently 7 g COOH-PEG-NH2 (small additions). The system was left under stirring under inert flow for about 90 h.

From the 3-necked flask, the yellow solution is transferred into a 2L 1-necked flask and washed with 100 mL chloroform.

The product was concentrated to about 550 ml (distillate volume CHCl3=650 ml) by means of a rotavapor. The product is transferred from the 2 L flask to the 1 L 1-necked flask (washing with 250 mL CHCl₃).

The copolymer was precipitated and washed with 250 mL (×5) of cold diethyl ether: at the beginning, the suspension must be added slowly and shaken with a glass rod to prevent over-saturation. At each wash, the system was rested in an ice bath and then the supernatant was removed (opalescent suspension containing quaternary salts and unreacted organic impurities).

The white solid of rubbery appearance was washed with 250 mL (×5) deionized water to remove traces of unreacted COOH-PEG-NH₂.

The system was put under vacuum (liquid ring pump first and oil pump thereafter), alternating vacuum drying (oil pump-trap at −30° C.), disintegration of the polymer to facilitate drying and storage in a freezer overnight. The procedure is repeated until no more weight loss is observed.

The product is stored in a freezer.

86.80 g of polymer were recovered (yield of about 83%).

Example 7

Synthesis (PLGA-b-PEG-COOH 12-3 kDa)

Step 1: Activation of the Carboxylic Functionality with NHS

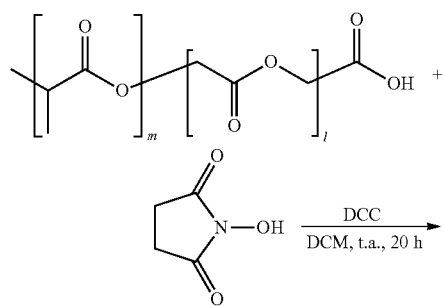

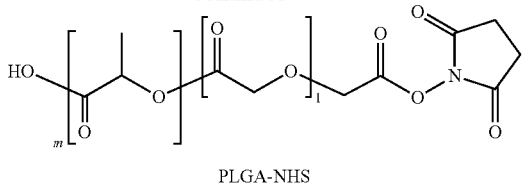

PLGA-NHS

Reagent Technical Specifications:
Reagents

| | |
|---|---|
| 7 g | PLGA-COOH 7000-17000 (50:50 Poly (DL-Lactide-co-glycolide), Carboxylate End Group) → 0.582 mmol |
| 150 mL | CH₂Cl₂ (Dichloromethane->99.9%) for solubilization of PLGA-COOH |
| 0.27 g | NHS (N-hydroxysuccinimide-98%) washed with 30 mL CH₂Cl₂ → 2.34 mmol |
| 0.51 g | DCC (N,N Dicyclohexylcarbodiimide-99%) washed with 50 mL CH₂Cl₂ → 2.493 mmol |
| 70 mL | CH₂Cl₂ (Dichloromethane >99.9% to wash the 500 mL flask before filtration on Buckner |
| 550 mL | Diethyl ether (Aldrich ≥99.8%) |

PLGA-COOH and 150 mL dichloromethane were added to a 500 m flask under nitrogen. After solubilization of the polymer, the NHS was added (30 mL CH₂Cl₂ for funnel washing) and then DCC was added—consecutive additions—50 mL CH₂Cl₂ for funnel washing.

The system was left under stirring for about 24 hours in an inert atmosphere. The colorless solution (with white solid in suspension) was filtered on Buckner into a 1 L tailed flask in order to remove dicyclohexylurea. The 500 mL flask was washed with 70 ml CH₂Cl₂.

The product was transferred to a pear-shaped 1-necked flask and concentrated by a Buchi rotavapor, after about 1 h, a thick white suspension was obtained.

Step 2: Conjugation of PLGA-NHS with NH2-PEG-COOH

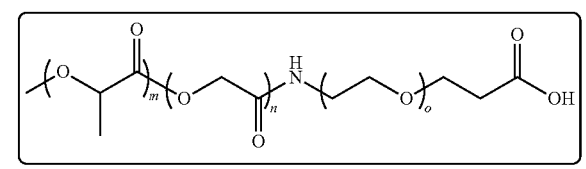

Reagents
PLGA-NHS (Reaction Intermediate) in Thick Suspension

| | |
|---|---|
| 260 mL | CHCl₃ (Chloroform-Aldrich ≥99.5%-Cat) for intermediate |
| 20 mL | CHCl₃ for amino PEG COOH washing |
| 0.35 mL | DIPEA (N,N-Diisopropylethylamine 99.5%) |
| 1.82 g | COOH-PEG-NH₂ (Polymer-hydrochloride form ratio) → 0.6066 mmol |
| 520 mL | Diethyl ether (≥99.8%) |
| 300 mL | Deionized water |

Process

In a 500 mL flask under nitrogen, intermediate 100 (×2) and 60 mL CHCl3 were solubilized. 0.35 mL DIPEA were added to the system using a syringe and subsequently 1.82 g COOH-PEG-NH2 with 20 mL funnel washing CHCl3). The system was left under stirring under inert flow for 96 h.

From the 4-necked flask the suspension, filtered on Buckner for the presence of brown and white residues, was transferred to a 500 mL 1-necked flask washing with a few mL chloroform.

The product is concentrated (Volume CHCl3 distillate=170 mL) by means of a rotavapor. 120 mL cold diethyl ether (white suspension-rubbing of glass rod-ice bath), 60 mL (white suspension-ice bath), 80 mL (beginning of precipitation-ice bath), 60 mL (freezer for about 1 hour) are added to the yellow solution. The product was washed with 100 mL (×2) cold diethyl ether. At each wash, the system was rested in freezer and then the supernatant was removed (opalescent suspension containing quaternary salts and unreacted organic impurities). The three fractions in ether were dried (1.20 g).

The white solid of rubbery appearance was washed with 100 mL (×3) deionized water (ice bath) to remove traces of unreacted COOH-PEG-NH2.

The copolymer (18.10 g) was placed under vacuum in Buchi rotavapor and was then connected to the oil pump (ethanol-dry ice trap) for about 4 h (7.78 g—drying alternating with disintegration). The product was subjected to disintegration and then placed under vacuum, alternating stages of drying, disintegration and freezer. The procedure is repeated until no more weight loss is observed.

The product is stored in a freezer.

7.52 g of polymer were recovered (yield of 88%-86%).

(2 g) P.M.:11300 g/mol—0.1769 mmol (5 g) P.M.:15400 g/mol—0.3246 mmol mmol PLGA COOH: 0.5015 g PLGA PEG COOH $(mol_{2g}*P.M._{2g})$ $(mol_{5g}*P.M._{5g})=2.529+5.972=8.5$ g

Calculations with PM=12000. Expected 8.74 g PLGA PEG COOH

Example 8

Setup of the Nanobioreactor (NBR)

Reagents:

40.0 g Fe3O4-DDA equal to 9.5e-04 mol $Fe_3O_4$; 220.0 mg PLGA-b-PEG-COOH equal to 5e-06 mol polymer; 400 ml phosphate buffer 1 mM After having solubilized 220.0 mg polymer in 5 mL THF, 40.0 g Fe3O4-DDA are injected in the organic solution. Using a 60 mL syringe, the product is concentrated in a rotavapor to remove the THF present. The process is stopped when there is no longer formation and condensation of organic vapors.

The product is then concentrated and dialyzed with Cogent M system with a Pellicon 2mini 100 kDa membrane, according to the following procedure: Once the system has been drained, the suspension of NBR, concentrated by a theoretical factor of 1.5 and then dialyzed with 2000 mL UP water buffered $10^{-3}$M is introduced.

It is further concentrated to a volume of 100 mL in Pellicon XL system with a 500 kDa membrane after keeping the system in NaOCl 1:10 for 30 minutes.

The process is stopped once the theoretical concentration factor of 20× has been reached (theoretical conc. of inorganic: 1.0%).

It is then filtered with Millipore Sterivex 0.22 μm filters in PES. It is stored in refrigerator.

Characterization

DLS

| Sample | PDI | Z-ave | V-mean | % (volume peak) | notes |
|---|---|---|---|---|---|
| NBR | 0.125 | 43.10 (±0.61) | 34.55 (±1.30) | 100 | After filtration |

Zpotential

| Sample | Zpot | % (Z peak) | Notes |
|---|---|---|---|
| NBR | −43.2 | 100 | After filtration |

ICP

| Sample | Fe % | % $Fe_3O_4$ | mMolarity |
|---|---|---|---|
| NBR | 0.735 | 1.015 | 43.84 |

Stability in Culture Medium:

the sample is diluted to 1:20 (0.05% wt inorganic phase) in DMEM+10% FBS+glutamine+antibiotic: it is clear without aggregates.

DLS

| Sample | PDI | Z-ave | V-mean | % (volume peak) |
|---|---|---|---|---|
| NBR (20X) culture medium | 0.161 | 139.60 (±1.06) | 143.20 (±3.06) | 100 |

Example 9

Continuous Nanobioreactor Production (NBR)

Reagents:

200 mg PLGA-b-PEG-COOH equal to 4.4e-06 mol polymer; 52.6 g THF; 36.4 g Fe3O4-DDA equal to 8.6e-04 mol $Fe_3O_4$; 1000 mL $H_2O$ MilliQ with phosphate buffer at pH 7.4=$10^{-3}$M.

To a 100 mL Erlenmeyer flask, 0.2 g polymer PLGA-b-PEG-COOH and 52.6 g THF are added, stirring until complete dissolution (several minutes). Finally, 36.4 g Fe3O4-DDA are added.

Synthesis:

A double peristaltic pump system was set up after calibration to perform the addition of the organic solution in aqueous stream (THF/water volume ratio=1/10). The respective tubes draw the solution directly from the lungs containing the THF solution (with PLGA-b-PEG-COOH and particles) and the phosphate buffer solution prepared in 2.5 L bottle.

The product is first stripped in a rotavapor to remove the THF and then brought to dryness; once the volatile component has evaporated, the product is recovered.

The product is then concentrated and dialyzed with Cogent M system with Pellicon
2mini 100 kDa membrane.

Emptying the system, 254.5 g product are recovered.
Theoretical concentration factor: 4.7×
Theoretical concentration: 0.078%
Time needed for concentration and dialysis: 20'.

The product is further concentrated in Pellicon XL with 500 kDa membrane. Time needed to final concentration: 1 h.

Recovered: 11.51 g net of the dead volume inside the membrane about 1-2 mL. Theor. Conc. (considering the $V_{dead}$ 1.5 mL): 14%

Characterization

DLS

| Sample | PDI | Z-ave | V-mean | % (volume peak) | notes |
| --- | --- | --- | --- | --- | --- |
| NBR | 0.125 | 41.8 (+0.4) | 34.2 (+0.9) | 100 | After concentration in Pellicon XL; diluted 0.05% in buffer | for stability tests in serum at 0.05% (theoretical)

ICP

| Sample | Fe % | % Fe$_3$O$_4$ | mMolarity |
| --- | --- | --- | --- |
| NBR | 1.078 | 1.490 | 64.35 |

Example 10

Set Up of Targeted Nanobioreactor with moAb (NBR_hERG)

Reagents:

40.38 mL NBR equal to 0.533 μmol-COOH; 2.32 mL Sulfo-NHS 0.23 mM solution equal to 0.533 μmol; 190 μL EDAC*HCl 28 mM solution equal to 0.053 mmol; 2.64 mL 1.52 mg/mL hERG solution equal to 4.0 mg hERG (2.7e-08 mol); 1500 mL aqueous solution of Na$_2$HPO$_3$=10$^{-3}$M To a sterile 250 mL vessel, 40.38 mL NBR are added and then 0.19 mL EDAC (0.028 M) and 2.32 mL Sulfo-NHS are added. After 40' (at rest), 2.64 mL of the hERG1 solution (1.52 mg/mL=4.0 mg) are diluted with 15.52 mL phosphate buffer 1 mM and this is added to 42.89 mL activated NBR. ($V_{final}$=61.05 mL; Fe$_3$O$_4$=0.056%). It is left to rest overnight.

The system is set up for the dialysis of the product using the Pellicon XL 500 kDa membrane in PES. The system is washed with 300 mL H$_2$O MilliQ, 400 mL of 0.5% sodium hypochlorite are flown and the system is left to sterilize for about 30 min. It is then washed with 400 mL buffer 1 mM.

The product is then concentrated to a volume of 22 mL, setting the pump speed to about 15 mL/min (P=0.27 bar). Also the first dialysis permeate is analyzed via BCA® test.

It is dialyzed with 100 mL (4 volumes) of buffer 1 mM at a speed of 15 mL/min (P=0.27 bar) and concentrated to a volume of 4.7 mL.

Finally, the product is filtered with 0.22 μM filters in PES. It is stored in refrigerator.

The product thus obtained exhibits a good stability after dilution in culture medium at 0.05% wt; there are no aggregates or solid forms in flocculation visible to the naked eye.

Characterization

DLS

| Sample | PDI | Z-ave | V-mean | % (volume peak) | notes |
| --- | --- | --- | --- | --- | --- |
| NBR_hERG | 0.157 | 66.14 (±0.30) | 50.79 (±0.32) | 100 | End product |

Zpotential

| Sample | Zpot | % (Z peak) | Notes |
| --- | --- | --- | --- |
| NBR_hERG | −40.0 | 100 | End product |

ICP

| Sample | Fe % | % Fe$_3$O$_4$ | mMolarity |
| --- | --- | --- | --- |
| NBR_hERG | 0.226 | 0.312 | 13.465 |

Stability:

DLS

| Sample | PDI | Z-ave | V-mean | % (volume peak) | notes |
| --- | --- | --- | --- | --- | --- |
| NBR_hERG | 0.179 | 136.7 (±0.7) | 137.6 (±8.4) | 100 | End product |

BCA Test

For the execution of the BCA test, the concentration of NBR_hERG is normalized with respect to that of the corresponding antibody-free (NBR), which therefore serves as a white. Once the staining has developed by the addition of the relevant reagent, the samples are analyzed by UV-vis spectrophotometer, then the absorbance values are interpolated on the calibration curve previously prepared (using a BSA standard) and the equivalent moAb concentrations is extrapolated. The net amount of antibody present on the NBR_hERG is calculated by subtracting the values of moAb found in the eluate and in the white (NBR) from that corresponding to the sample of NBR_hERG. See equation below:

$$C_{moAb(NBR\_moAb)}\text{net}=C_{moAb(NBR\_moAb)}-C_{moAb(NBR)}-C_{moAb(eluate)}$$

The following are the experimental values measured:

mAb Eluate=45 μg/mL mAb NBR=435 μg/mL mAb NBR_hERG=863 μg/mL

Actual mAb (mAb NBR_hERG−mAb NBR)=428 μg/mL

Ratio mAb/Fe$_3$O$_4$=0,14

Example 11

Set Up of Targeted Nanobioreactor with Fluo-Dyes (NBR_Fluo)

Reagent Technical Specifications:

| | |
|---|---|
| NBR | $[Fe_3O_4]$ = 0.081% [PLGA-b-PEG-COOH] = 0.061%* |
| 1,4-diaminobutane | MW = 88.15 g/mol d = 0.877 g/mL |
| Alexa Fluor ® 750 (750 nm) | MW = 1300 g/mol |
| Phosphate buffer in $H_2O$ UP | C = 1M; pH 7.4 |

Reagents:

| | |
|---|---|
| 30.00 mL NBR | (0.40 μmol PPGC43-3.1) |
| 1 mg Alexa Fluor 750 | (in 770 μL → [1 mM]) |
| 1500 mL $H_2O$ MilliQ with phosphate buffer at 7.4 = | $10^{-3}$M |
| Sulfo-NHS | MW = 217.13 g/mol |
| EDAC•HCl | MW = 191.7 g/mol |

Preparation of Fluo-NH2 solution

The fluorophore is solubilized with 770 μL DMSO obtaining a solution 1 nmol/μL.

In a 12-mL vial, 4950 μL 1 mM phosphate buffer are added and 50 μL of the fluorophore Alexa Fluor 750 solution (50 nmol) are added. It is then placed under magnetic stirring and then 100 μL of solution 132 μg/mL 1,4-diaminobutane are added (corresponding to 150 nmol=13.2 g). The solution is left to react for 24 h, in the dark and under nitrogen flow. The NH2-terminal fluorophore thus obtained will be used for the subsequent synthesis step without being purified.

Preparation of the Sulfo-NHS solution (0.23 mM)

Weigh exactly 5.0 mg of Sulfo-NHS and solubilize in a 100 mL flask using 1 mM phosphate buffer.

Preparation of the EDAC solution (0.028 mM)

To a 4 mL vial, 2.7 mg EDAC and 0.5 mL 1 mM buffer are added. Cap and shake to facilitate mixing. This solution must be prepared immediately before the reaction.

Synthesis:

To a 100 mL vessel, 30.00 mL NBR DF are added and 0.14 mL EDAC (0.028 M) and 1.72 mL Sulfo-NHS (0.23 mM) are added.

Total volume: 30.00 mL+0.14 mL+1.72 mL=31.86 mL

After 40' (at rest), 2.64 mL of the Alexa Fluor 750 solution (10 nmol/mL) are added.

It is left to rest for 4 h.

A control DLS is performed (NBR_Fluo TQ).

Purification:

The system is set up for the dialysis of the product using a Pellicon XL 500 kDa membrane in PES and a peristaltic pump Masterflex L/S with easy-load II head. The system is then sterilized fluxing sodium hypochlorite at 0.5% and leaving to react for about 30 min. After washing with sterile MilliQ water and setting up the system with 1 mM phosphate buffer (also sterile), the product is concentrated to a volume of 10 mL (collect 23 ml of permeate) setting the pump speed to about 12 mL/min (P=0.25 mbar). A rate of the first permeate is retained for the UV-VIS analysis. It is then dialyzed with 40 mL (4 volumes) of buffer 1 mM working at a speed of 12 mL/min (P=0.25 mbar). At this point, it is concentrated to a volume of 6 mL.

Recovered: 5.00 g

Theoretical synthesis concentration factor: 5.8×

Theoretical concentration factor compared to NBR: 5×

Filtration:

The product is filtered with 0.22 μM Millex filters in PES. For the purification of the entire product, one filter is needed. It is stored in refrigerator.

NBR_27_Fluo_01 DF recovered=4.49 g Characterization

DLS

R0366/2013; R0368/2013

| Sample | PDI | Z-ave | V-mean | % | notes |
|---|---|---|---|---|---|
| NBR_Fluo | 0.147 | 55.14 (±0.59) | 42.03 (±1.59) | 100 | DF, dil. 1:10 in buffer 1 mM |

Z potential

R0368/2013

| Sample | Zpot | Zwidth | Cond | % Z | QF | Notes |
|---|---|---|---|---|---|---|
| NBR_Fluo | −42.0 | 18.3 | 0.233 | 100 | 2.28 | DF, dil. 1:10 in buffer 1 mM |

ICP

R0368/2013

| Sample | Fe % | % $Fe_3O_4$ | mMolarity |
|---|---|---|---|
| NBR_Fluo | 0.243 | 0.336 | 14.532 |

UV-Vis

R0368/2013

| Sample | Abs | ε | Conc. (nmol/L) | % linked |
|---|---|---|---|---|
| Eluate NBR_Fluo | 0.125575 | 242000 | 558 | 27.1 |

Example 12

Set Up of Targeted Nanobioreactor with Fluo-Dyes (NBR_Fluo)

Reagent Technical Specifications:

| | |
|---|---|
| NBR | $[Fe_3O_4]$ = 0.081% [PPGC43-3.1] = 0.061%* |
| 1,4-diaminobutane | MW = 88.15 g/mol d = 0.877 g/mL |
| Alexa Fluor 750 (750 nm) | MW = 1300 g/mol |
| Phosphate buffer in H2O UP | C = 1M; pH 7.4 |

Reagents:

| | |
|---|---|
| 30.00 mL NBR | (0.40 μmol PPGC43-3.1) |
| 50.00 nmol Cyanine 5-1,4-diaminobutane | (in 5.0 mL → [10 μM]) |
| 1500 mL $H_2O$ MilliQ with phosphate buffer at 7.4 = | $10^{-3}$M |
| Sulfo-NHS | MW = 217.13 g/mol |
| EDAC•HCl | MW = 191.7 g/mol |

Preparation of Fluo-NH2 solution

To a 12 mL vial, 5 mL 1 mM phosphate buffer, 50 nmol (1 bottle) Cyanine 5, NHS-ester and then 150 nmol (13.2 g) 1,4-diaminobutane are added. The solution is left to react for 24 h, in the dark, under magnetic stirring and nitrogen flow. The NH2-terminal fluorophore thus obtained will be used for the subsequent synthesis step without being purified.

nitrogen flow. The NH2-terminal fluorophore thus obtained will be used for the subsequent synthesis step without being purified.

Preparation of the Sulfo-NHS solution (0.23 mM)

Weigh exactly 5.0 mg of Sulfo-NHS and solubilize in a 100 mL flask using 1 mM phosphate buffer.

Preparation of the EDAC solution (0.028 mM)

To a 4 mL vial, 2.7 mg EDAC and 0.5 mL buffer 1 mM are added. Cap and shake to facilitate mixing. This solution must be prepared immediately before the reaction.

Synthesis:

To a 50 mL sterile vessel, 30.00 mL NBR are added and 0.14 mL EDAC (0.028 M) and 1.72 mL Sulfo-NHS (0.23 mM) are added.

Total volume: 30.00 mL+0.14 mL+1.72 mL=31.86 mL

After 40' (at rest), 2.64 mL of the Cyanin-5-$NH_2$ solution (10 nmol/mL) are added. It is left to rest for 4 h.

Purification:

The system is set up for the dialysis of the product using the Pellicon XL 500 kDa membrane in PES.

At this point, the product is concentrated to a volume of 10 mL (collect 23 mL permeate). Setting the pump speed to about 12 mL/min (P=0.25 mbar); t=4' Retain a rate of the first permeate for the UV-VIS analysis.

Dialyze with 40 mL (4 volumes) of buffer 1 mM. v 12 mL/min (P=0.25 mbar); t=11'

At this point, it is concentrated to a volume of 6 mL; t=5'.

Recovered: 4.29 g

Theoretical synthesis concentration factor: 5.5×

Theoretical concentration factor compared to NBR: 4.8×

Filtration:

The product is filtered with 0.22 μM Millex filters in PES. For the purification of the entire product, one filter is needed. It is stored in refrigerator.

NBR_Fluo recovered=4.11 g

Example 13

Production of Targeted Nanobioreactor with moAb and Fluo-Dyes (NBR_hERG-Fluo)

Reagent Technical Specifications:

| NBR | [$Fe_3O_4$] = 0.821% [PPGC43-3.1] = 0.616% |
| --- | --- |
| 1,4-diaminobutane | MW = 88.15 g/mol d = 0.877 g/mL |
| Cyanine 5-NHS ester | (650 nm) |
| Phosphate buffer in $H_2O$ UP | C = 1M; pH 7.4 |
| Sulfo-NHS | MW = 217.13 g/mol |
| EDAC•HCl | MW = 191.7 g/mol |
| hERG1 | MW = 15000 g/mol |

Reagents:

| 4.79 mL NBR | (0.64 μmol PPGC43-3.1) |
| --- | --- |
| 25 nmol Cyanine 5-NHS ester | (in 2.5 mL → [10 μM]) |
| 2.7 mg EDAC | |
| 5.0 mg Sulfo-NHS | |
| 4.8 mg hERG | (3.2 mL → 1500 μg/ml) |
| 1500 mL $H_2O$ MilliQ with phosphate buffer at pH 7.4 | [ ] = $10^{-3}$M |

Preparation of Fluo-NH2 solution

To a 12 mL vial, 5 mL 1 mM phosphate buffer, 50 nmol (1 bottle) Cyanine 5 NHS-ester are added, place under magnetic stirring and then add 100 μL of 13.2 mg/100 mL solution of 1,4-diaminobutane (corresponding to 150 nmol=13.2 μg). The solution is left to react for 24 h, in the dark and under nitrogen flow. The NH2-terminal fluorophore thus obtained will be used for the subsequent synthesis step without being purified.

Preparation of the Sulfo-NHS solution (0.23 mM)

Weigh exactly 5.0 mg of Sulfo-NHS and solubilize in a 100 mL flask using 1 mM phosphate buffer.

Preparation of the EDAC solution (0.028 mM)

To a 4 mL vial, 2.7 mg EDAC and 0.5 mL buffer 1 mM are added. Cap and shake to facilitate mixing. This solution must be prepared immediately before the reaction.

Synthesis:

To a sterile 100 mL vessel, 7.95 mL buffer 1 mM and then 4.79 mL NBR are added. The mixture is stirred gently to mix and then 2.29 mL EDAC (0.028 M) and 2.79 mL Sulfo-NHS (0.23 mM) are added.

Total volume: 7.95 mL+4.79 mL+2.29 mL+2.79 mL=17.83 mL

After 40' (at rest), 2.5 mL of the Cyanin 5-NH5 ester solution (10 nmol/mL) are added. 3.2 mL of the hERG1 solution (1.5 mg/mL=4.8 mg) are then diluted in 52.32 mL phosphate buffer 1 mM and added to the suspension containing activated NBR and fluorophore. It is left to rest overnight.

Purification:

The system is set up for the dialysis of the product using the Pellicon XL 500 kDa membrane in PES already used for NBR_19. Wash with 300 mL $H_2O$ MilliQ, then flux with 400 mL of 0.5% sodium hypochlorite and leave in hypochlorite for about 30 min. Wash the system with 400 mL buffer 1 mM.

At this point, the product is concentrated to a volume of 20 mL (collect 50 mL permeate). Setting the pump speed to about 14 mL/min (P=0.2 mbar); t=15' Retain a rate of the first permeate for the BCA test.

Dialyze with 80 mL (4 volumes) of buffer 1 mM. v 14 mL/min (P=0.2 mbar); t=16'

At this point, it is concentrated to a volume of 10 mL; t=4'.

Recovered: 6.46 g

Theoretical dilution factor compared to NBR: 1.3×

Filtration:

The product is filtered with 0.22 μM Millex filters in PES. For the purification of the entire product, one filter is needed. It is stored in refrigerator.

NBR_hERG-Fluo recovered=7.79 g

Characterization

DLS

| Sample | Dates | PDI | Z-ave | V-mean | % | notes |
|---|---|---|---|---|---|---|
| NBR_hERG1-Fluo | 15-feb | 0.118 | 47.39 (±0.28) | 38.25 (±0.89) | 100 | DF, dil 1:10 in buff. 1 mM |
| NBR_hERG1-Fluo DMEM | 15-feb | 0.176 | 155.4 (±11.8) | 171.5 (±19.4) | 100 | DF, dil 1:10 in DMEM All In |

Z Potential

| Sample | Dates | Zpot | Zwidth | Cond | % Z | QF | Notes |
|---|---|---|---|---|---|---|---|
| NBR_19_hERG1_Fluo_01 DF | 15-feb | −42.4 | 7.4 | 0.256 | 100 | 2.26 | DF, dil. 1:10 in buffer 1 mM |

ICP

| Sample | Fe % | % $Fe_3O_4$ | mMolarity |
|---|---|---|---|
| NBR_hERG1-Fluo | 0.320 | 0.442 | 19.081 |

Example 14

Production of Nanobioreactor Loaded with Active Ingredient (NBR_PTX and NBR_hERG_PTX)

Reagent Technical Specifications:

| | |
|---|---|
| PPGC43-3.1 (batch 5-A) | 50:50 Mw = 43000; PEG Mw 3000 |
| Fe3O4-DDA | [$Fe_3O_4$] = 0.55% |
| PTX | Discovery Fine Chemicals |
| Phosph. buffer 1 mM | pH = 7.4 |
| THF | d = 0.89 |
| Reagents: | |
| 35.6 g Fe3O4-DDA (40.0 mL) (195.8 mg $Fe_3O_4$) | 490 mg/L (in water) |
| 212.6 mg PPGC43-3.1 | 490 mg/L (in water) |
| 21.2 mg PTX | |
| 400 ml phosph. buffer 1 mM (actual: 440 mL) | |
| 60 mL syringe 25G needle | |

Preparation of the THF solution [with PLGA-PEG (5.5 mg/g), PTX (0.55 mg/g) and $Fe_3O_4$ (5.5 mg/g)]

212.6 mg PPGC43-3.1 are solubilized in 4 mL (4 mL vial) THF and 21.2 mg PTX in 2.12 mL THF (4 mL vial) and this is added to 35.6 g $Fe_3O_4$-DDA in a 100 mL flask Synthesis:

The THF solution is stacked in 400 ml of phosphate buffer 1 mM using a 60 ml syringe with 25 G needle.

NBR_PTX obtained: 455.8 g

Stripping

The product is treated in a rotavapor to remove the THF present. To this end, it is moved to a 1000 mL flask and the following conditions are set:

Bath T 40°

Pressure: 154 mbar

Revolutions: 80 rpm

After 1 h, once the evaporation of the volatile component has finished, the product is recovered and weighed.

NBR_PTX Rotavap recovered=418.22 g (37.58 g THF removed)

Dialysis and Concentration:

The product is concentrated and dialyzed with AMICON system with a 50 kDa membrane, according to the following procedure:

1) wash with 50 mL osmotized $H_2O$ to remove the impurities in the membrane
2) system wash with solution with 50 mL phosphate buffer in $H_2O$ UP, $10^{-3}$M.

Once the system has been drained, NBR_PTX is added and concentrated to about 100 mL Thereafter, 4 washings are carried out with 150 mL buff. 1 mM. Finally, it is concentrated to 75 mL discarding 45 mL eluate.

Emptying the system, 59.40 g of product (NBR_PTX) are recovered.

Theoretical concentration factor=7.7×

Filtration:

The product is filtered with a Millipore Sterivex 0.22 μM filter in PES (cylindrical filters).

Characterization

DLS

| Sample | PDI | Z-ave | V-mean | % | notes |
|---|---|---|---|---|---|
| NBR_PTX | 0.174 | 53.55 (±0.58) | 41.66 (±0.55) | 100 | DC, dil. 1:10 in buffer 1 mM |

ICP

| Sample | Fe % | % $Fe_3O_4$ | mMolarity |
|---|---|---|---|
| NBR_PTX | 0.347 | 0.480 | 20.716 |

Stability:

The concentrated sample diluted 1:8 in DMEM+10% FBS+glutamine+antibiotic: is limpid without aggregates

DLS

R0211/2013

| Sample | Dates | PDI | Z-ave | V-mean1 | % | notes |
|---|---|---|---|---|---|---|
| NBR_PTX DMEM A1 | 08-may | 0.155 | 126.1 (±2.2) | 121.8 (±4.6) | 100 | DC, dil. 1:8 in DMEM All In |

PTX Analysis

| Sample | PTX:PLGA-PEG ratio | FWR % | LC % | LE % | PTX mg/mL |
|---|---|---|---|---|---|
| NBR_PTX_10 | 1:10 | 5.5 | 2.1 | 40.0 | 142.57 |

Example 15

Production of Nanobioreactor Loaded with Active Ingredient (NBR_PT-X and NBR_hERG_PTX)

Reagent Technical Specifications:

| | |
|---|---|
| NBR_PTX | [Fe$_3$O$_4$] = 0.48% [PPGC43-3.1] = 0.36% * |
| Phosphate buffer in H$_2$O UP | C = 1M; pH 7.4 |
| Sulfo-NHS | MW = 217.13 g/mol |
| EDAC | MW = 155.24 g/mol d = 0.877 g/mL |
| hERG | MW = 150000 g/mol |

Reagents:

| | |
|---|---|
| 4.26 mL NBR_PTX_p10 DF | (3.33 * 10$^{-4}$ μmol PPGC43-3.1) |
| 5.0 mg Sulfo-NHS | (in 100 mL → [0.23 mM]) |
| 20 μL EDAC | (in 4 mL → [28 mM]) |
| 2.5 mg hERG | (0.833 mL * 3 mg/mL) |
| 1500 mL phosphate buffer at pH 7.4 | [ ] = 10$^{-3}$M |

Preparation of the Sulfo-NHS solution (0.23 mM)

Weigh 5.0 mg of Sulfo-NHS and solubilize in a 100 mL flask using 1 mM phosphate buffer.

Preparation of the EDAC solution (0.028 mM)

To a 4 mL vial, 2.7 mg EDAC and 0.5 mL buffer 1 mM are added. Cap and shake to facilitate mixing. This solution must be prepared immediately before the reaction.

Synthesis:

To a sterile 40 mL vessel, 2.36 mL buffer 1 mM and then 4.26 mL NBR_PTX are added. The mixture is stirred gently to mix and then 1.19 mL EDAC (0.028 M) and 1.45 mL Sulfo-NHS are added.

Total volume: 2.36 mL+4.26 mL+1.19 mL+1.45 mL=9.26 mL

After 40' (at rest), the HERG1 solution obtained by diluting 0.833 mL of the hERG1 solution (3 mg/mL) with 27.25 mL buffer 1 mM is added. ($V_{final}$=37.34 mL; Fe$_3$O$_4$=0.056%).

It is left to rest overnight.

Purification:

The system is set up for the dialysis of the product using the Pellicon XL 500 kDa membrane in PES. Wash with 300 mL H$_2$O MilliQ, then flux with 400 mL of 0.5% sodium hypochlorite and leave in hypochlorite for about 30 min. Wash the system with 400 mL buffer 1 mM.

At this point, the product is concentrated to a volume of 13 mL (collect 25 mL permeate). Setting the pump speed to about 13 mL/min (P=0.2 mbar); t=5'

Retain a rate of the first permeate for the BCA test.

Dialyze with 60 mL (4 volumes) of buffer 1 mM. v 13 mL/min (P=0.2 mbar); t=14'

At this point, it is concentrated to a volume of 10 mL; t=10'.

Recovered: 7.40 g

Theoretical synthesis concentration factor: 5.5×

Theoretical dilution factor Compared to NBR_PTX: 2.8×

Filtration:

The product is filtered with 0.22 μm Sterivex filters in PES. For the purification of the entire product, one filter is needed. It is stored in refrigerator.

NBR_PTX recovered=6.88 g

Characterization

DLS

| Sample | Dates | PDI | Z-ave | V-mean | % | notes |
|---|---|---|---|---|---|---|
| NBR_PTX | 26-oct | 0.138 | 63.62 (±0.58) | 50.58 (±0.60) | 100 | DF, diluted 1:10 in buff. 1 mM |

Zpotential

| Sample | Dates | Zpot | Zwidth | Cond | % Z | QF | Notes |
|---|---|---|---|---|---|---|---|
| NBR_PTX | 26-oct | −37.3 | 13.8 | 0.231 | 100 | 2.17 | DF, diluted 1:10 in buff. 1 mM |

ICP

| Sample | Fe % | % Fe₃O₄ | mMolarity |
| --- | --- | --- | --- |
| NBR_PTX | 0.191 | 0.264 | 11.400 |

Actual yield of the process=94.5%

Example 16

Incorporation of NBR in Lymphocytes

T cells and Jurkat cells are capable of incorporating the nano particles with a method developed by the applicants. T cells/Jurkat cells are loaded with NP at a concentration of 0.05% in a suitable specific culture medium (medium). In order to form the medium containing the NP, the NP are dispensed first and then the specific culture medium. The medium is made up as follows:

RPMI 1640 MEDIUM, w 2.0 g/L NaHCO3—w/o L-Glutamine. (BIOCHROM) (code: F1215)-500 mL added with:

L-GLUTAMINE, solution 200 mM (100×). (EUROCLONE) (code: ECB 3000D)—5.5 mL without dilution SODIUM PYRUVATE, 100 mM (100×). (Gibco) (code: 11360-039)-5.5 mL without dilution MEM NEAA Minimum essential medium Non-Essential Aminoacids (100×). (Gibco) (code: 11140-035)-5.5 mL without dilution GENTOMIL (gentamicin) 80 mg/2 ml (AIC N° 029314059)-1 2 mL vial 2-MERCAPTOETHANOL. (Merck) (code: 444203)—use 5.5 mL 2-Mercaptoethanol as follows: 37 µl 2-MERCAPTOETHANOL in 99.963 mL sterile H2O (final vol 100 mL)

10% fetal bovine serum FBS: Fetal Bovine Serum, Qualified. (Sigma-Aldrich) (code: F6178)

Where necessary, autologous serum of the patient or media in the absence of serum will be used instead of fetal bovine serum.

The invention claimed is:

1. A human immune system cell containing a construct, said construct comprising:
   a structural center comprising a clustered plurality of magnetite nanoparticles, wherein the surface of each of the plurality of nanoparticles in the cluster is functionalized with catechol to provide hydrophobic reactivity to said clustered plurality of nanoparticles, and
   a biocompatible polymeric matrix encapsulating the structural center, wherein a molecule having therapeutic action is optionally dispersed in said biocompatible polymeric matrix.

2. The cell according to claim 1, wherein the structural center of the construct comprises a clustered plurality of magnetite nanoparticles and gold nanorods.

3. The cell according to claim 1, wherein said biocompatible polymeric matrix of the construct consists of biodegradable copolymers.

4. The cell according to claim 3, wherein said biodegradable copolymers are selected from: biodegradable nanomicelles, polyesters, polyurethanes, polycarbonates, poly(glutamic acid), polyetheramine, and polybenzylglutamate.

5. The cell according to claim 4, wherein said biodegradable nanomicelles consist of poly(lactic-co-glycolic) acid and polyethylene glycol carboxylate (PLGA-b-PEG-COOH), having formula (I)

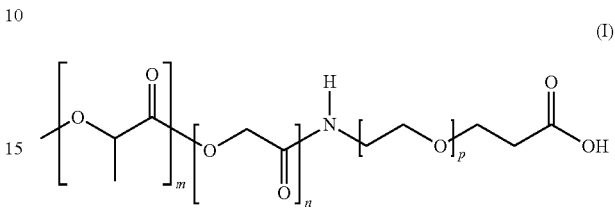

(I)

wherein m=[117-330]; n=[117-330]; p=[60-100].

6. The cell according to claim 1, wherein said molecule having therapeutic action of the construct is selected from: an anticancer agent, a peroxynitrite scavenger, a superoxydismutase inhibitor, a retinoid, a cytokine, and aspirin.

7. The cell according to claim 5, wherein the end carboxyl group of the fragment PEG-COOH of the nanomicelles is further functionalized with monoclonal antibodies, proteins, peptides or active molecules for specific recognition by the cellular over-expressions.

8. The cell according to claim 7, wherein said antibodies are selected from: hEGR, hEGFR, IgG, moAb.

9. A process for preparing the according to claim 1, said process comprising:
   providing
      an organic solution comprising: the polymers of the polymeric matrix, the magnetite nanoparticles functionalized with catechol and a solvent, and
      an aqueous solution of Na₂HPO₄ 1 mM; and
   mixing the organic solution with the aqueous solution in a constant flow in a mixing cell using batch or continuous synthesis.

10. The cell according to claim 5, wherein the end carboxyl group of the fragment PEG-COOH is activated so as to promote subsequent esterification of amino end groups.

11. The cell according to claim 1, wherein said cell is selected from the group consisting of:
T-lymphocytes, monocytes, macrophages, dendritic cells, natural killer cells, B-lymphocytes, neutrophil granulocytes, eosinophil granulocytes, basophil granulocytes, and gamma delta cells.

12. An MRI imaging agent comprising:
a cell according to claim 1.

13. The cell according to claim 1, wherein said cell is selected from the group consisting of:
T-lymphocytes, monocytes, macrophages, dendritic cells, natural killer cells, B-lymphocytes, neutrophil granulocytes, eosinophil granulocytes, basophil granulocytes, and gamma delta cells.

14. An MRI and photoacoustic spectrometry imaging agent comprising: the cell according to claim 1.

* * * * *

UNITED STATES PATENT AND TRADEMARK OFFICE
CERTIFICATE OF CORRECTION

Page 1 of 1

PATENT NO. : 10,888,630 B2
APPLICATION NO. : 15/110189
DATED : January 12, 2021
INVENTOR(S) : Giovanni Baldi et al.

It is certified that error appears in the above-identified patent and that said Letters Patent is hereby corrected as shown below:

In the Claims

In Claim 9, at Column 30, Line 31, delete "A process for preparing the according to claim 1" and insert --A process for preparing the construct according to claim 1-- in its place.

Signed and Sealed this
Third Day of August, 2021

Drew Hirshfeld
*Performing the Functions and Duties of the*
*Under Secretary of Commerce for Intellectual Property and*
*Director of the United States Patent and Trademark Office*